United States Patent
Lujan et al.

(10) Patent No.: US 11,944,821 B2
(45) Date of Patent: *Apr. 2, 2024

(54) SYSTEM AND METHOD TO ESTIMATE REGION OF TISSUE ACTIVATION

(71) Applicant: The Cleveland Clinic Foundation, Cleveland, OH (US)

(72) Inventors: J. Luis Lujan, Mayfield Heights, OH (US); Ashutosh Chaturvedi, Powell, OH (US); Cameron McIntyre, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/203,044

(22) Filed: Mar. 16, 2021

(65) Prior Publication Data
US 2021/0220656 A1    Jul. 22, 2021

Related U.S. Application Data

(63) Continuation of application No. 16/431,581, filed on Jun. 4, 2019, now Pat. No. 10,981,013, which is a (Continued)

(51) Int. Cl.
*A61N 1/36* (2006.01)
*A61N 1/05* (2006.01)
(Continued)

(52) U.S. Cl.
CPC ..... *A61N 1/36185* (2013.01); *A61N 1/37252* (2013.01); *G06N 20/00* (2019.01);
(Continued)

(58) Field of Classification Search
CPC ............ A61N 1/37252; A61N 1/36185; A61N 1/0534; A61N 1/36082; G06N 20/00;
(Continued)

(56) References Cited

U.S. PATENT DOCUMENTS 3,999,555 A   12/1976  Person
4,144,889 A   3/1979   Tyers et al.
(Continued)

FOREIGN PATENT DOCUMENTS

EP   1048320   11/2000
EP   1166819   1/2002
(Continued)

OTHER PUBLICATIONS

Role of electrode design on the volume of tissue activated during deep brain stimulation Butson et al. (Year: 2006).*
(Continued)

*Primary Examiner* — Kakali Chaki
*Assistant Examiner* — Ababacar Seck
(74) *Attorney, Agent, or Firm* — Branch Partners PLLC; Bruce E. Black

(57) ABSTRACT

A computer-implemented method for determining the volume of activation of neural tissue. In one embodiment, the method uses one or more parametric equations that define a volume of activation, wherein the parameters for the one or more parametric equations are given as a function of an input vector that includes stimulation parameters. After receiving input data that includes values for the stimulation parameters and defining the input vector using the input data, the input vector is applied to the function to obtain the parameters for the one or more parametric equations. The parametric equation is solved to obtain a calculated volume of activation.

18 Claims, 10 Drawing Sheets

Related U.S. Application Data continuation of application No. 13/839,906, filed on Mar. 15, 2013, now Pat. No. 10,360,511, which is a continuation of application No. 12/869,159, filed on Aug. 26, 2010, now Pat. No. 8,589,316.

(60) Provisional application No. 61/237,375, filed on Aug. 27, 2009.

(51) Int. Cl.

| | | |
|---|---|---|
| *A61N 1/372* | (2006.01) | |
| *G06F 18/214* | (2023.01) | |
| *G06F 18/2411* | (2023.01) | |
| *G06N 5/025* | (2023.01) | |
| *G06N 7/01* | (2023.01) | |
| *G06N 20/00* | (2019.01) | |
| *G16H 20/30* | (2018.01) | |
| *G16H 20/40* | (2018.01) | |
| *G16H 50/50* | (2018.01) | |

(52) U.S. Cl.
CPC ............ *G16H 50/50* (2018.01); *A61N 1/0534* (2013.01); *A61N 1/36082* (2013.01); *G06F 18/214* (2023.01); *G06F 18/2411* (2023.01); *G06N 5/025* (2013.01); *G06N 7/01* (2023.01); *G16H 20/30* (2018.01); *G16H 20/40* (2018.01)

(58) Field of Classification Search
CPC ........ G06N 5/025; G06N 7/005; G16H 50/50; G16H 20/30; G16H 20/40; G06K 9/6256; G06K 9/6269
See application file for complete search history.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,778,238 A | 7/1998 | Hofhine |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,895,416 A | 4/1999 | Barreras, Sr. et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,330,466 B1 | 12/2001 | Hofmann et al. |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,470,207 B1 | 10/2002 | Simon et al. |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,526,415 B2 | 2/2003 | Smith et al. |
| 6,539,263 B1 | 3/2003 | Schiff et al. |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,754,374 B1 | 6/2004 | Miller et al. |
| 6,778,846 B1 | 8/2004 | Martinez et al. |

(56) References Cited

U.S. PATENT DOCUMENTS

| | | |
|---|---|---|
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,873,872 B2 | 3/2005 | Gluckman et al. |
| 6,892,090 B2 | 5/2005 | Verard et al. |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 6,993,384 B2 | 1/2006 | Bradley et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault, Jr. et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | DiLorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,520,848 B2 | 4/2009 | Schneider et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,445 B1 | 5/2012 | Moffitt |
| 8,180,601 B2 | 5/2012 | Butson et al. |
| 8,195,300 B2 | 6/2012 | Gliner et al. |
| 8,209,027 B2 | 6/2012 | Butson et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 9,235,685 B2 | 1/2016 | McIntyre et al. |
| 2001/0029509 A1 | 10/2001 | Smith et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0013951 A1 | 1/2003 | Stefanescu et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0199944 A1* | 10/2003 | Chapin ............... G06N 3/061 607/48 |
| 2003/0212439 A1 | 11/2003 | Schuler et al. |
| 2003/0216630 A1 | 11/2003 | Jersey-Willuhn et al. |
| 2003/0228042 A1 | 12/2003 | Sinha |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0092809 A1 | 5/2004 | DeCharms |
| 2004/0096089 A1 | 5/2004 | Borsook et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |

(56) References Cited

U.S. PATENT DOCUMENTS

| | | |
|---|---|---|
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0205566 A1 | 9/2005 | Kassayan |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1* | 4/2007 | Butson .............. A61N 1/0534 600/407 |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0266280 A1 | 11/2007 | Ng et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1* | 6/2008 | McIntyre .............. A61N 1/0531 382/128 |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0062886 A1 | 3/2009 | O'Handley et al. |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1* | 8/2009 | McIntyre .............. A61N 1/36146 703/11 |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2009/0306741 A1* | 12/2009 | Hogle .............. A61N 1/36103 600/595 |
| 2009/0312817 A1* | 12/2009 | Hogle .............. A61B 5/682 607/54 |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Butson et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0218818 A1 | 9/2011 | Butson et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0027272 A1 | 2/2012 | Akinyemi et al. |

(56) References Cited

U.S. PATENT DOCUMENTS

| | | |
|---|---|---|
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2012/0330622 A1 | 12/2012 | Butson et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | | |
|---|---|---|---|
| EP | 1372780 | | 1/2004 |
| EP | 1372780 A2 | | 1/2004 |
| EP | 1559369 | | 8/2005 |
| WO | 97/39797 | | 10/1997 |
| WO | 98/48880 | | 11/1998 |
| WO | 01/90876 | | 11/2001 |
| WO | 02/26314 | | 4/2002 |
| WO | 02/28473 | | 4/2002 |
| WO | 02/065896 | | 8/2002 |
| WO | 02065896 A2 | | 8/2002 |
| WO | 02/072192 | | 9/2002 |
| WO | 03/086185 | | 10/2003 |
| WO | 03086185 A1 | | 10/2003 |
| WO | 2004/019799 A2 | | 3/2004 |
| WO | 2004041080 | | 5/2005 |
| WO | 2006017053 | | 2/2006 |
| WO | 2006017053 A1 | | 2/2006 |
| WO | 2006113305 | | 10/2006 |
| WO | 20071097859 | | 8/2007 |
| WO | 20071097861 A1 | | 8/2007 |
| WO | 2007/100427 | | 9/2007 |
| WO | 2007/100428 | | 9/2007 |
| WO | 07/115120 A2 | | 10/2007 |
| WO | 2007/112061 | | 10/2007 |
| WO | WO-2008035344 A2 * | 3/2008 | ......... A61N 1/36082 |
| WO | 2009097224 | | 8/2009 |
| WO | 2010/ 120823 A2 | | 10/2010 |
| WO | 2011025865 | | 3/2011 |
| WO | 2011/139779 A1 | | 11/2011 |
| WO | 2011/159688 A2 | | 12/2011 |
| WO | 2012088482 | | 6/2012 |

OTHER PUBLICATIONS

Patient-Specific Analysis of the Volume of Tissue Activated During Deep Brain Stimulation Butson et al (Year: 2007).*
Current steering to control the volume of tissue activated during deep brain stimulation Butson et al. (Year: 2008).*
Johnson. M. D., et al., "Repealed voltage biasing improves unit recordings by reducing resistive tissue impedances," IEEE Transactions on Neural Systems and Rehabilitation Engineering [see also IEEE Trans. on Rehabilitation Engineering] (2005), pp. 160-165.
Jones, DK., et al., "Optimal strategies for measuring diffusion in anisotropic systems by magnetic resonance imaging," Magn. Reson. Med., 42(3) (Sep. 1999), pp. 515-525.
Khan, et al., "A Sequence Independent Power-on-Reset Circuit for Multi-Voltage Systems," Jan. 2006, pp. 1271-1274.
Kitagawa, M., et al., "Two-year follow-up of chronic stimulation of the posterior subthalamic white matter for tremor-dominant Parkinson's disease," Neurosurgery, 56(2) (Feb. 2005), pp. 281-289.
Krack, P., et al., "Postoperative management of subthalamic nucleus stimulation for Parkinson's disease," Mov. Disord., vol. 17(suppl 3) (2002), pp. 188-197.
Le Bihan, D, et al., "Diffusion tensor imaging: concepts and applications," J Magn Reson Imaging, 13(4) (Apr. 2001), pp. 534-546.
Lee, DC., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10 (3 Suppl 1) (Aug. 1997), pp. 231-237.
Limousin, P., et al., "Electrical stimulation of the subthalamic nucleus in advanced Parkinson's disease," N Engl J Med., 339(16)(Oct. 15, 1998), pp. 1105-1111.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mayberg, H. S., et al., "Deep brain stimulation for treatment-resistant depression," Neuron, 45(5) (Mar. 3, 2005), pp. 651-660.
McIntyre. C. C., et al., "Extracellular stimulation of central neurons: influence of stimulus waveform and frequency on neuronal output," J_ Neurophysiol., 88(4), (Oct. 2002), pp. 1592-1604.
McIntyre, Cameron , et al., "Finite element analysis of the current-density and electric field generated by metal microelectrodes," Ann Biomed Eng., 29(3), (2001), pp. 227-235.
McIntyre, C. C., et al., "How does deep brain stimulation work? Present understanding and future questions," J Clin Neurophysiol., 21(1), (Jan.-Feb. 2004), pp. 40-50.
McIntyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
McIntyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cat. No. 02CH37392) IEEEPiscataway, NJ (2002), pp. 2047-2048.
McIntyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001 ), pp. 806-809.
McIntyre, C. C., et al., "Model-based design of stimulus waveforms for selective microstimulation in the central nervous system," Proceedings of the First Joint [Engineering in Medicine and Biology, 1999, 21st Annual Conf. and the 1999 Annual FallMeeting of the Biomedical Engineering Soc.] BM ES/EMBS Conference, vol. 1 (1999), p. 384.
McIntyre, Cameron C., et al., "Modeling the excitability of mammalian nerve fibers: influence of afterpotentials on the recovery cycle," J Neurophysiol, 87(2) (Feb. 2002), pp. 995-1006.
McIntyre, Cameron C., et al., "Selective microstimulation of central nervous system neurons," Annals of biomedical engineering, 28(3) (Mar. 2000), pp. 219-233.
McIntyre, C. C., et al., "Sensitivity analysis of a model of mammalian neural membrane," Biol Cybern., 79(1) (Jul. 1998), pp. 29-37.
McIntyre, Cameron C., et al., "Uncovering the mechanism(s) of action of deep brain stimulation: activation, inhibition, or both," Clin Neurophysiol, 115(6) (Jun. 2004), pp. 1239-1248.
McIntyre. Cameron C .. et al., "Uncovering the mechanisms of deep brain stimulation for Parkinson's disease through functional imaging, neural recording, and neural modeling," Crit Rev Biomed Eng., 30(4-6) (2002), pp. 249-281.

(56) References Cited

OTHER PUBLICATIONS

McIntyre, Cameron C., et al., "Cellular effects of deep brain stimulation: model-based analysis of activation and inhibition," J Neurophysiol, 91(4) (Apr. 2004), pp. 1457-1469.
McIntyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
McIntyre, Cameron C., et al., "Electric field generated by deep brain stimulation of the subthalamic nucleus," Biomedical Engineering Society Annual Meeting, Nashville TN (Oct. 2003), 16 pages.
McIntyre, Cameron C., et al., "Computational analysis of deep brain stimulation," Expert Review of Medical Devices, vol. 4, No. 5, Sep. 1, 2007, pp. 615-622, London, GB.
McIntyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Merrill, D. R, et al., "Electrical stimulation of excitable tissue: design of efficacious and safe protocols," J Neurosci Methods, 141(2) (Feb. 15, 2005), pp. 171-198.
Micheli-Tzanakou, E., et al., "Computational Intelligence for target assessment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miocinovic, S., et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Miocinovic, S., et al., "Sensitivity of temporal excitation properties to the neuronal element activated by extracellular stimulation," J Neurosci Methods, 132(1) (Jan. 15, 2004), pp. 91-99.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Montgomery, E B., et al., "Mechanisms of deep brain stimulation and future technical developments," Neurol Res., 22(3) (Apr. 2000), pp. 259-266.
Moro, E, et al., "The impact on Parkinson's disease of electrical parameter settings in STN stimulation," Neurology, 59(5) (Sep. 10, 2002), pp. 706-713.
Moss, J., et al., "Electron microscopy of tissue adherent to explanted electrodes in dystonia and Parkinson's disease," Brain, 127(Pt 12) (Dec. 2004), pp. 2755-2763.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. L Evidence from selective inactivation of cell bodies and axon initial segments," Exp. Brain Res., 118(4) (Feb. 1998), pp. 489-500.
Nowinski, W. $_L$, et al., "Statistical analysis of 168 bilateral subthalamic nucleus implantations by means of the probabilistic functional atlas," Neurosurgery, 57(4 Suppl) (Oct. 2005), pp. 319-330.
Obeso, J. A., et al., "Deep-brain stimulation of the subthalamic nucleus or the pars interna of the globus pallidus in Parkinson's disease," N Engl J Med., 345(13), The Deep-Brain Stimulation for Parkinson's Disease Study Group (Sep. 27, 2001 ), pp. 956-963.
O'Suilleabhain, PE., et al., "Tremor response to polarity, voltage, pulsewidth and frequency of thalamic stimulation," Neurology, 60(5) (Mar. 11, 2003), pp. 786-790.
Patrick, S. K., et al., "Quantification of the UPDRS rigidity scale," IEEE Transactions on Neural Systems and Rehabilitation Engineering [see also IEEE Trans. on Rehabilitation Engineering], 9(1) (2001), pp. 31-41.
Phillips, M. D., et al., "Parkinson disease: pattern of functional MR imaging activation during deep brain stimulation of subthalamic nucleus—initial experience," Radiology, 239(1) (Apr. 2006), pp. 209-216.
Pierpaoli, C, et al., "Toward a quantitative assessment of diffusion anisotropy," Magn Reson Med., 36(6) (Dec. 1996), pp. 893-906.
Plaha, P., et al., "Stimulation of the caudal zona incerta is superior to stimulation of the subthalamic nucleus in improving contralateral parkinsonism," Brain, 129 (Pt 7) (Jul. 2006), pp. 1732-1747.
Plonsey, R, et al., "Considerations of quasi-stationarity in electrophysiological systems," Bull Math Biophys., 29(4) (Dec. 1967), pp. 657-664.
Ranck. J B .. ""Specific impedance of rabbit cerebral cortex."" Exp. Neurol.. vol. 7 (Feb. 1963). pp. 144-152.
Ranck. J B.. et al.. "The Specific impedance of the dorsal columns of the cat: an anisotropic medium." Exp. Neurol.. 11 (Apr. 1965). pp. 451-463.
Ranck. J B. "Which elements are excited in electrical stimulation of mammalian central nervous system: a review," Brain Res .. 98(3) (Nov. 21, 1975). pp. 417-440.
Rattay. F. et al.. "A model of the electrically excited human cochlear neuron. I. Contribution of neural substructures to the generation and propagation of spikes." Hear Res .. 153(1-2) (Mar. 2001 ). pp. 43-63.
Rattay. F. "A model of the electrically excited human cochlear neuron. II. Influence of the three-dimensional cochlear structure on neural excitability." Hear Res .. 153(1-2) (Mar. 2001). pp. 64-79.
Rattay. F. ""Analysis of models for external stimulation of axons."" IEEE Trans. Biomed. Eng .. vol. 33 (1986). pp. 974-977.
Rattay. F. ""Analysis of the electrical excitation of CNS neurons."" IEEE Transactions on Biomedical Engineering. 45(6) (Jun. 1998). pp. 766-772.
Rattay. F. ""Arrival at Functional Electrostimulation by modelling of fiber excitation."" Proceedings of the Ninth annual Conference of the IEEE Engineering in Medicine and Biology Society (1987). pp. 1459-1460.
Rattay. F. "The influence of intrinsic noise can preserve the temporal fine structure of speech signals in models of electrically stimulated human cochlear neurones." Journal of Physiology. Scientific Meeting of the Physiological Society. London. England. UK Apr. 19-21, 1999 (Jul. 1999). p. 170P.
Rizzone. M. et al.. ""Deep brain stimulation of the subthalamic nucleus in Parkinson's disease: effects of variation in stimulation parameters."" J_ Neurol. Neurosurg. Psychiatry . 71(2) (Aug. 2001). pp. 215-219.
Rose. T. L.. et al.. "'Electrical stimulation with Pt electrodes. VIII. Electrochemically safe charge injection limits with 0.2 ms pulses [neuronal application].'" IEEE Transactions on Biomedical Engineering. 37(11) (Nov. 1990). pp. 1118-1120.
Rubinstein. J_ T., et al., "Signal coding in cochlear implants: exploiting stochastic effects of electrical stimulation," Ann Otol Rhinol Laryngol Suppl., 191 (Sep. 2003), pp. 14-19.
Saint-Cyr, J A., et al., "Localization of clinically effective stimulating electrodes in the human subthalamic nucleus on magnetic resonance imaging," J_ Neurosurg., 97(5) (Nov. 2002), pp. 1152-1166.
Sances, A, et al., "In Electroanesthesia: Biomedical and Biophysical Studies," A Sances and SJ Larson, Eds., Academic Press, NY (1975), pp. 114-124.
Schwan, H.P., et al., "The conductivity of living tissues," Ann NY Acad Sci., 65(6) (Aug. 1957), pp. 1007-1013.
Sotiropoulos, P. N., et al., "A biophysical model of deep brain stimulation of the subthalamic nucleus," Society for Neuroscience Meeting, 1011.5 (2004), 1 page.

(56) References Cited

OTHER PUBLICATIONS

Sl. Jean, P, et al., "Automated atlas integration and interactive three-dimensional visualization tools for planning and guidance in functional neurosurgery," IEEE Transactions on Medical Imaging, 17(5) (1998), pp. 672-680.

Starr, PA., et al., "Implantation of deep brain stimulators into the subthalamic nucleus: technical approach and magnetic resonance imaging-verified lead locations," J_ Neurosurg., 97(2) (Aug. 2002), pp. 370-387.

Sterio, D, et al., "Neurophysiological refinement of subthalamic nucleus targeting," Neurosurgery, 50(1) (Jan. 2002), pp. 58-69.

Struijk, J_ J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F, et al., "Anatomo-clinical correlation of intraoperative stimulation-induced side-effects during HF-DBS of the subthalamic nucleus," Neurol Sci., vol. 23 (Suppl 2) (2002), pp. 109-110.

Tarler. M.. et al.. ""Comparison between monopolar and tripolar configurations in chronically implanted nerve cuff electrodes."" IEEE 17th Annual Conference Engineering in Medicine and Biology Society. vol. 2 (1995). pp. 1093-1094.

Taylor. R. S. et al.. ""Spinal cord stimulation for chronic back and leg pain and failed back surgery syndrome: a systematic review and analysis of prognostic factors."" Spine. 30(1) (Jan. 1, 2005). pp. 152-160.

Testerman. Roy L.. ""Coritical response to callosal stimulation: A model for determining safe and efficient stimulus parameters."" Annals of Biomedical Engineering. 6(4) (1978). pp. 438-452.

Trost. M.. et al.. ""Network modulation by the subthalamic nucleus in the treatment of Parkinson's disease."" Neuroimage. 31(1) (May 15, 2006). pp. 301-307.

Tuch. D S.. et al.. "'Conductivity mapping of biological tissue using diffusion MRI.'" Ann NY Acad Sci .. 888 (Oct. 30, 1999). pp. 314-316.

Tuch. D S.. et al.. "'Conductivity tensor mapping of the human brain using diffusion tensor MRI.'" Proc Natl Acad Sci USA. 98(20) (Sep. 25, 2001). pp. 11697-11701.

Tyler. R. S. et al.. "Update on bilateral cochlear implantation." Curr Opin Otolaryngol Head Neck Surg . 11 (5) (Oct. 2003). pp. 388-393.

Veraart. C.. et al.. "'Selective control of muscle activation with a multipolar nerve cuff electrode.'" IEEE Transactions on Biomedical Engineering. 40(7) (Jul. 1993). pp. 640-653.

Vercueil. L et al.. "Deep brain stimulation in the treatment of severe dystonia." J_ Neurol.. 248(8) (Aug. 2001 ). pp. 695-700.

Vidailhet. M.. et al.. "'Bilateral deep-brain stimulation of the globus pallidus in primary generalized dystonia.'" N Engl J Med . 352(5) (Feb. 3, 2005). pp. 459-467.

Vilalte. "'Circuit Design of the Power-on-Reset.'" Apr. 2000. pp. 1-25.

Viola, P., et al., "Alignment by maximization of mutual information," International Journal of Computer Vision, 24(2) (1997), pp. 137-154.

Vitek, J L., "Mechanisms of deep brain stimulation: excitation or inhibition," Mov. Disord., vol. 17 (Suppl. 3) (2002), pp. 69-72.

Voges, J, et al., "Bilateral high-frequency stimulation in the subthalamic nucleus for the treatment of Parkinson disease: correlation of therapeutic effect with anatomical electrode position," J_ Neurosurg., 96(2) (Feb. 2002), pp. 269-279.

Volkmann, J., et al., "Basic algorithms for the programming of deep brain stimulation in Parkinson's disease," Mov Disord., 21 Suppl 14 (Jun. 2006), pp. S284-S289.

Volkmann, J, et al., "Introduction to the programming of deep brain stimulators," Mov. Disord., vol. 17 (Suppl 3) (2002), pp. 181-187.

Wakana, S, et al., "Fiber tract-based atlas of human white mailer anatomy," Radiology, 230(1) (Jan. 2004), pp. 77-87.

Walter, B. L., et al., "Surgical treatment for Parkinson's disease," Lancet Neural., 3(12) (Dec. 2004), pp. 719-728.

Warman, EN., et al., "Modeling the effects of electric fields on nerve fibers: Determination of excitation thresholds," IEEE Transactions on Biomedical Engineering, 39(12) (1992), pp. 1244-1254.

Wei, X. F., et al., "Current density distributions, field distributions and impedance analysis of segmented deep brain stimulation electrodes," J Neural Eng., 2(4) (Dec. 2005), pp. 139-147.

Wu, YR., et al., "Does Stimulation of the GPi control dyskinesia by activating inhibitory axons?," Mov. Disord., vol. 16 (2001 ), pp. 208-216.

Yelnik, J, et al., "Localization of stimulating electrodes in patients with Parkinson disease by using a three-dimensional atlas-magnetic resonance imaging coregistration method," J Neurosurg., 99(1) (Jul. 2003), pp. 89-99.

Yianni, John, et al., "Globus pallidus internus deep brain stimulation for dystonic conditions: a prospective audit," Mov. Disord., vol. 18 (2003), pp. 436-442.

Zonenshayn, M, et al., "Comparison of anatomic and neurophysiological methods for subthalamic nucleus targeting," Neurosurgery, 47(2) (Aug. 2000), pp. 282-294.

Zonenshayn, M., et al., "Location of the active contact within the subthalamic nucleus (STN) in the treatment of idiopathic Parkinson's disease," Surg Neural., 62(3) (Sep. 2004), pp. 216-225.

McIntyre, C. C., et al., "Computational analysis of deep brain stimulation," Expert Review of Medical Devices, vol. 4, No. 5 (Sep. 1, 2007), pp. 616-620, Future Drugs Lid., London, GB.

Eaton, H., "Electric field induced in a spherical volume conductor from arbitrary coils: application to magnetic stimulation and MEG," Medical & Biological Engineering & Computing (Jul. 1992), pp. 433-440.

Cooper. S, et al., "Differential effects of thalamic stimulation parameters on tremor and paresthesias in essential tremor," Movement Disorders, 17 (Supp. 5), (2002), p. S193.

Cover, T.M. et al., "Elements of information theory," (1991) John Wiley & Sons, New York, NY, pp. 1-542.

Coubes, P, et al., "Treatment of DYT1-generalised dystonia by stimulation of the internal globus pallidus," Lancet, 355(9222), (Jun. 24, 2000), pp. 2220-2221.

Dasilva, A.F. M., et al., "A Primer Diffusion Tensor Imaging of Anatomical Substructures," Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput Sci. vol. (2717), Springer-Verlag Berlin, Germany (2003), pp. 142-150.

Finnis, K W., et al., "3-D functional atalas of subcortical structures for image guided stereotactic neurosurgery," Neuroimage, vol. 9, No. 6, Iss. 2 (1999), p. S206.

Finnis, K W., et al., "3D Functional Database of Subcorticol Structures for Surgical Guidance in Image Guided Stereotactic Neurosurgery," Medical Image Computing and Computer-Assisted Intervention—MICCAI'99, Second International Conference,Cambridge, UK, Sep. 19-22, 1999, Proceedings (1999), pp. 758-767.

Finnis, K W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.

Finnis, K W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

Finnis, K W., et al., "Application of a Population Based Electrophysiological Database to the Planning and Guidance of Deep Brain Stereotactic Neurosurgery," Proceedings of the 5th International Conference on Medical Image Computing andComputer-Assisted Intervention—Part II, Lecture Notes in Computer Science; vol. 2489 (2002), pp. 69-76.

Finnis, K W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.

(56) References Cited

OTHER PUBLICATIONS

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Foster, K. R., et al., "Dielectric properties of tissues and biological materials: a critical review," Crit Rev Biomed Eng., 17(1) (1989), pp. 25-104.
Gabriels, L, et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Geddes, L.A., et al., "The specific resistance of biological material—a compendium of data for the biomedical engineer and physiologist," Med Biol Eng., 5(3) (May 1967), pp. 271-293.
Gimsa, J., et al., "Choosing electrodes for deep brain stimulation experiments—electrochemical considerations," J Neurosci Methods, 142(2) (Mar. 30, 2005), pp. 251-265.
Goodall, E V., et al., "Modeling study of activation and propagation delays during stimulation of peripheral nerve fibers with a tripolar cuff electrode," IEEE Transactions on Rehabilitation Engineering, [see also IEEE Trans. on Neural Systems andRehabilitation], 3(3) (Sep. 1995), pp. 272-282.
Goodall, E V., et al., "Position-selective activation of peripheral nerve fibers with a cuff electrode," IEEE Transactions on Biomedical Engineering, 43(8) (Aug. 1996), pp. 851-856.
Goodall, E V., "Simulation of activation and propagation delay during tripolar neural stimulation," Proceedings of the 15th Annual International Conference of the IEEE Engineering in Medicine and Biology Society (1993), pp. 1203-1204.
Grill, W. M., et al., "Deep brain stimulation creates an informational lesion of the stimulated nucleus," Neuroreport., 15(7) (May 19, 2004), pp. 1137-1140.
Grill, WM., et al., "Electrical properties of implant encapsulation tissue," Ann Biomed Eng., vol. 22 (1994), pp. 23-33.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neural Res., 22(3) (Apr. 2000), pp. 247-258.
Guridi et al. "The subthalamic nucleus, hemiballismus and Parkinson's disease: reappraisal of a neurological dogma," Brain, vol. 124, 2001, pp. 5-19.
Haberler. C, et al., "No tissue damage by chronic deep brain stimulation in Parkinson's disease," Ann Neural., 48(3) (Sep. 2000), pp. 372-376.
Hamel, W, et al., "Deep brain stimulation of the subthalamic nucleus in Parkinson's disease: evaluation of active electrode contacts," J Neural Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Hardman, C. D., et al., "Comparison of the basal ganglia in rats, marmosets, macaques, baboons, and humans: volume and neuronal number for the output, internal relay, and striatal modulating nuclei," J Comp Neural., 445(3) (Apr. 8, 2002), pp. 238-255.
Hashimoto, T., et al., "Stimulation of the subthalamic nucleus changes the firing pattern of pallidal neurons," J Neurosci., 23(5) (Mar. 1, 2003), pp. 1916-1923.
Haslinger, B., et al., "Frequency-correlated decreases of motor cortex activity associated with subthalamic nucleus stimulation in Parkinson's disease," Neuroimage, 28(3) (Nov. 15, 2005), pp. 598-606.
Haueisen, J, et al., "The influence of brain tissue anisotropy on human EEG and MEG," Neuroimage, 15(1) (Jan. 2002), pp. 159-166.
Hemm, S. et al., "Deep brain stimulation in movement disorders: stereotactic coregistration of two-dimensional electrical field modeling and magnetic resonance imaging," J Neurosurg., 103(6) (Dec. 2005), pp. 949-955.
Hemm, S., et al., "Evolution of Brain Impedance in Dystonic Patients Treated by GPi Electrical Stimulation," Neuromodulation, 7(2) (Apr. 2004), pp. 67-75.
Hershey, T., et al., "Cortical and subcortical blood flow effects of subthalamic nucleus stimulation in PD," Neurology, 61(6) (Sep. 23, 2003), pp. 816-821.
Herzog, J., et al., "Most effective stimulation site in subthalamic deep brain stimulation for Parkinson's disease," Mov Disord., 19(9) (Sep. 2004), pp. 1050-1054.
Hines, $M_L$, et al., "The NEURON simulation environment," Neural Comput, 9(6) (Aug. 15, 1997), pp. 1179-1209.
Hodaie, M, et al., "Chronic anterior thalamus stimulation for intractable epilepsy," Epilepsia, 43(6) (Jun. 2002), pp. 603-608.
Hoekema, R, et al., "Multigrid solution of the potential field in modeling electrical nerve stimulation," Comput Biomed Res., 31(5) (Oct. 1998), pp. 348-362.
Holsheimer, J., et al., "Chronaxie calculated from current-duration and voltage-duration data," J Neurosci Methods, 97(1) (Apr. 1, 2000), pp. 45-50.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001 ), pp. 429-434.
Zhang, Y., et al., "Atlas-guided tract reconstruction for automated and comprehensive examination of the white matter anatomy," Neuroimage 52(4) (2010), pp. 1289-1301.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.

(56) References Cited

OTHER PUBLICATIONS

Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Mayberg, H. S., et al., "Limbic-cortical dysregulation: a proposed model of depression," J Neuropsychiatry Clin Neurosci. 9 (3) (1997), pp. 471-481.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
McIntyre, C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Bazin et al., "Free Software Tools for Atlas-based Volumetric Neuroimage Analysis", Proc. SPIE 5747, Medical Imaging 2005: Image Processing, 1824 May 5, 2005.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102(5) pp. 363-367 May 1993.
Viola, et al., "Importance-driven focus of attention," IEEE Trans Vis Comput Graph 12 (5) (2006), pp. 933-940.
Mayr et al., "Basic Design and Construction of the Vienna FES Implants: Existing Solutions and Prospects for New Generations of Implants", Medical Engineering & Physics, 2001; 23:53-60.
Dawant, B. M., et al., "Computerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Gross, RE., et al., "Advances in neurostimulation for movement disorders," Neurol Res., 22(3) (Apr. 2000), pp. 247-258.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Miocinovic et al., "Stereotactive Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Wakana, S., et al., "Fiber tract-based atlas of human white matter anatomy," Radiology, 230(1) (Jan. 2004), pp. 77-87.
Voghell et al., "Programmable Current Source Dedicated to Implantable Microstimulators" ICM '98 Proceedings of the Tenth International Conference, pp. 67-70.
Jones et al., "An Advanced Demultiplexing System for Physiological Stimulation", IEEE Transactions on Biomedical Engineering, vol. 44 No. 12 Dec. 1997, pp. 1210-1220.
Mouine et al. "Multi-Strategy and Multi-Algorithm Cochlear Prostheses", Biomed. Sci. Instrument, 2000; 36:233-238.
Exploring Connectivity of the Brain's White Matter with Dynamic Queries, Anthony Sherbondy, David Akers, Rachel Mackenzie, Robert Dougherty, and Brian Wandell (Year: 2005).
Official Communication for U.S. Appl. No. 13/839,906 dated Apr. 21, 2015.
Official Communication for U.S. Appl. No. 13/839,906 dated Sep. 14, 2018.
Official Communication for U.S. Appl. No. 13/839,906 dated Oct. 5, 2016.
Official Communication for U.S. Appl. No. 13/839,906 dated May 18, 2016.
Official Communication for U.S. Appl. No. 13/839,906 dated Oct. 15, 2015.
Official Communication for U.S. Appl. No. 16/431,581 dated Nov. 3, 2020.
Cameron C. McIntyre et al. "Excitation of Central Nervous System Neurons by Nonuniform Electric Fields" Department of Biomedical Engineering, Case Western Reserve University, Biophysical Journal vol. 76, Feb. 1999, 878-888.
"BioPSE: The Biomedical Problem Solving Environment," http://www.sci.utah.edu/cibc/software/index.html, NCRR Center for Integrative biomedical Computing (2004), 5 pages.
"Deep-brain stimulation of the subthalamic nucleus or the pars interna of the globus pallidus in Parkinson's disease," N Engl J Med., 345(13), Author: Deep-Brain Stimulation for Parkinson's Disease Study Group (Sep. 27, 2001), pp. 956-963.
European Patent Office, International Search Report and Written Opinion in International Application No. PCT/US2005/023672, dated Jan. 20, 2006, 19 Pages.
European Patent Office, International Search Report and the Written Opinion in International Application No. PCT/US09/66821, dated Aug. 31, 2010, 19 pages.
European Patent Office, International Search Report and the Written Opinion in International Application No. PCT/US2010/046772, dated Nov. 23, 2010, 17 pages.
"U.S. Appl. No. 10/885,982, Restriction Requirement dated Nov. 2, 2005," 6 pgs.
"U.S. Appl. No. 10/885,982, Response filed Feb. 2, 2006 to Restriction Requirement dated Nov. 12, 2005," 18 pgs.
"U.S. Appl. No. 10/885,982, Non-Final Office Action dated Apr. 21, 2006," 20 pgs.
"U.S. Appl. No. 10/885,982, Response filed Jul. 21, 2006 to Non-Final Office Action dated Apr. 21, 2006," 24 pgs.
"U.S. Appl. No. 10/885,982, Final Office Action dated Dec. 12, 2006," 10 pgs.
"U.S. Appl. No. 10/885,982, Response filed Mar. 12, 2007 to Final Office Action dated Dec. 12, 2006," 26 pgs.
"U.S. Appl. No. 10/885,982, Non-Final Office Action dated Apr. 19, 2007," 17 pgs.
"U.S. Appl. No. 10/885,982, Interview Summary dated Apr. 19, 2007," 2 pgs.

(56) References Cited

OTHER PUBLICATIONS

"U.S. Appl. No. 10/885,982, Response filed Jul. 19, 2007 to Non-Final Office Action dated Apr. 19, 2007," 19 pgs.
"U.S. Appl. No. 10/885,982, Final Office Action dated Aug. 9, 2007," 8 pgs.
"U.S. Appl. No. 10/885,982, Notice of Allowance and Examiner's Amendment dated Oct. 5, 2007," 13 pgs.
"U.S. Appl. No. 10/885,982, Interview Summary and Proposed Claims dated Oct. 18, 2007," 14 pgs.
"U.S. Appl. No. 11/278,223 Response filed Jul. 15, 2008 to Non-Final Office Action dated Apr. 15, 2008," 10 pages.
"U.S. Appl. No. 11/278,223 Non-Final Office Action dated Apr. 15, 2008," 8 pages.
Adler, D E., et al., "The tentorial notch: anatomical variation, morphometric analysis, and classification in 100 human autopsy cases," J. Neurosurg., 96(6), (Jun. 2002), pp. 1103-1112.
Alexander, D C., et al., "Spatial transformations of diffusion tensor magnetic resonance images," IEEE Transactions on Medical Imaging, 20 (11), (2001), pp. 1131-1139.
Alo, K. M., et al., "New trends in neuromodulation for the management of neuropathic pain," Neurosurgery, 50(4), (Apr. 2002), pp. 690-704.
Andrews, R. J., "Neuroprotection trek—the next generation: neuromodulation I. Techniques—deep brain stimulation, vagus nerve stimulation, and transcranial magnetic stimulation," Ann NY Acad Sci. 993, (May 2003), pp. 1-13.
Andrews, R. J., "Neuroprotection trek—the next generation: neuromodulation II. Applications—epilepsy, nerve regeneration, neurotrophins," Ann NY Acad Sci., 993, (May 2003), pp. 14-24.
Ashby, P., et al., "Neurophysiological effects of stimulation through electrodes in the human subthalamic nucleus," Brain, 122 (Pt 10), (Oct. 1999), pp. 1919-1931.
Astrom, M., et al., "The effect of cystic cavities on deep brain stimulation in the basal ganglia: a simulation-based study," J Neural Eng., 3(2), (Jun. 2006), pp. 132-138.
Back, C., et al., "Postoperative Monitoring of the Electrical Properties of Tissue and Electrodes in Deep Brain Stimulation," Neuromodulation, 6(4), (Oct. 2003), pp. 248-253.
Baker, K. B., et al., "Evaluation of specific absorption rate as a dosimeter of MRI-related implant heating," J Magn Reson Imaging., 20 (2), (Aug. 2004), pp. 315-320.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R , et al., "Diffusion tensor imaging using single-shot SENSE-EPI," Magn Reson Med., 48(1), (Jul. 2002), pp. 128-136.
Basser, P J., et al., "MR diffusion tensor spectroscopy and imaging," Biophys J., 66(1), (Jan. 1994), pp. 259-267.
Basser, P J., et al., "New currents in electrical stimulation of excitable tissues," Annu Rev Biomed Eng., 2, (2000), pp. 377-397.
Bedard, C., et al., "Modeling extracellular field potentials and the frequency-filtering properties of extracellular space," Biophys J., 86(3), (Mar. 2004), pp. 1829-1842.
Benabid, A L., et al., "Chronic electrical stimulation of the ventralis intermedius nucleus of the thalamus as a treatment of movement disorders," J. Neurosurg., 84(2), (Feb. 1996), pp. 203-214.
Benabid, A L., et al., "Combined (thalamotoy and stimulation) stereotactic surgery of the VIM thalamic nucleus for bilateral Parkinson disease," Appl Neurophysiol, vol. 50, (1987), pp. 344-346.
Benabid, A. L., et al., "Future prospects of brain stimulation," Neurol Res., 22 (3), (Apr. 2000), pp. 237-246.
Benabid, A L., et al., "Long-term suppression of tremor by chronic stimulation of the ventral intermediate thalamic nucleus," Lancet, 337 (8738), (Feb. 16, 1991), pp. 403-406.
Brummer, S. B., et al., "Electrical Stimulation with Pt Electrodes: II—Estimation of Maximum Surface Redox (Theoretical Non-Gassing) Limits," IEEE Transactions on Biomedical Engineering, vol. BME-24, Issue 5, (Sep. 1977), pp. 440-443.
Butson, C. R., et al., "Deep Brain Stimulation of the Subthalamic Nucleus: Model-Based Analysis of the Effects of Electrode Capacitance on the Volume of Activation," Proceedings of the 2nd International IEEE EMBS, (Mar. 16-19, 2005), pp. 196-197.
Butson, C. R., et al., "Patient Specific Analysis of the volume of tissue activated during deep brain stimulation," NeuroImage, Academic Press, vol. 34, No. 2, Dec. 2, 2006, pp. 661-670.
Butson, C. R., et al., "Current Steering to Control the Volume of Tissue Activated During Deep Brain Stimulation," Brain Stimulation 1, 2008, pp. 7-15.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Butson, C. R., et al., "Deep brain stimulation interactive visualization system," Society for Neuroscience, vol. 898.7 (2005), 1 page.
Butson, C. R., et al., "Role of Electrode Design on the Volume of Tissue Activated During Deep Brain Stimulation," Journal of Neural Engineering, Mar. 1, 2006, vol. 3, No. 1, pp. 1-8.
Butson, C. R., et al., "Patient-specific models of deep brain stimulation: 3D visualization of anatomy, electrode and volume of activation as a function of the stimulation parameters," Soc Neurosci Abstr. 30, (2004), p. 1011.11.
Butson, C. R., et al., "StimExplorer: Deep Brain Stimulation Parameter Selection Software System," Acta Neurochir Suppl, Jan. 1, 2007, vol. 97, No. 2, pp. 569-574.
Butson, C. R., et al., "Sources and effects of electrode impedance during deep brain stimulation," Clinical Neurophysiology, vol. 117, (2006), pp. 447-454.
Butson, C. R., et al., "Tissue and electrode capacitance reduce neural activation volumes during deep brain stimulation," Clinical Neurophysiology, vol. 116, (2005), pp. 2490-2500.
Chaturvedi, et al., "Subthalamic Nucleus Deep Brain Stimulation: Accurate Axonal Threshold Prediction with Diffusion Tensor Based Electric Field Models," Engineering in Medicine and Biology Society, 2006, EMBS' 06 28th Annual International Conference of the IEEE, IEEE, Piscataway, NJ USA, Aug. 30, 2006, 4 pages.
Christensen, Gary E., et al., "Volumetric transformation of brain anatomy," IEEE Transactions on Medical Imaging, 16(6), (Dec. 1997), pp. 864-877.
McNaughtan et al., "Electrochemical Issues in Impedance Tomography", 1st World Congress on Industrial Process Tomography, Buxton, Greater Manchester, Apr. 14-17, 1999.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Jeon et al., A Feasibility Study of Optical Coherence Tomography for Guiding Deep Brain Probes, Journal of Neuroscience Methods, 154:96-101, Jun. 2006.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.
Olivier Commowick et al., "Using Frankenstein's Creature Paradigm to Build a Patient Specific Atlas," Sep. 20, 2009, Medical Image Computing and Computer-Assisted Intervention, pp. 993-1000.

(56) References Cited

OTHER PUBLICATIONS

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

Khan et al., "Assessment of Brain Shift Related to Deep Brain Stimulation Surgery", Sterreotact Funct. Neurosurg., 86:44-53, published online Sep. 2007.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

Machado et al., "Deep Brain Stimulation for Parkinson's Disease: Surgical Technique and Perioperative Management", Movement Disorders, 21 :S247-S258, Jun. 2006.

Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.

Moran et al., "Real-Time Refinement of Subthalamic Nucleous Targeting Using Bayesian Decision-Making on the Root Mean Square Measure", Movement Disorders, 21: 1425-1431, published online Jun. 2006.

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural. Neurosurg. Psychiatry, 76:1161-1163, Aug. 2005.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Yelnik et al., "A Three-Dimensional, Histological and Deformable Atlas of the Human Basal J Ganglia. I. Atlas Construction Based on Immunohistochemical and MRI Data", NeuroImage, 34:618,-638, Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Izad, Oliver, "Computationally Efficient Method in Predicating Axonal Excitation," Dissertation for Master Degree, Department of Biomedical Engineering, Case Western Reserve University, May 2009.

Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi:10.1007/BF01908075.

An, et al., "Prefrontal cortical projections to longitudinal columns in the midbrain periaqueductal gray in macaque monkeys," J Comp Neural 401 (4) (1998), pp. 455-479.

Meila, Marina, "Comparing Clusterings by the Variation of Information," Learning Theory and Kernel Machines (2003): 173-187.

Carmichael, S. T., et al., "Connectional networks within the orbital and medial prefrontal cortex of macaque monkeys," J Comp Neural 371 (2) (1996), pp. 179-207.

Croxson, et al., "Quantitative investigation of connections of the prefrontal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421(2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Schmidt et al. "Sketching and Composing Widgets for 3D Manipulation," Eurographics, Apr. 2008, vol. 27, No. 2, pp. 301-310.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol Psychiatry 15 (1) (2010), pp. 64-79.

Greenberg. et al., "Three-year outcomes in deep brain stimulation for highly resistant obsessive-compulsive disorder," Neuropsychopharmacology 31 (11) (2006), pp. 2384-2393.

Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.

Fisekovic et al., "New Controller for Functional Electrical Stimulation Systems", Med. Eng. Phys. 2001; 23:391-399.

\* cited by examiner

| | | |
|---|---|---|
| $\dfrac{x^2}{a^2}+\dfrac{y^2}{b^2}+\dfrac{z^2}{c^2}=1$ |  | ellipsoid |
| $\left(\left|\dfrac{x}{A}\right|^r+\left|\dfrac{y}{B}\right|^r\right)^{t/r}+\left|\dfrac{z}{C}\right|^t \leq 1$ |  | super ellipsoid |
| $x^4+2x^2y^2+4y^4-x^3-6x^2-xy^2 = 0$<br>$y^2 = p(x-a)(x-b)(x-c)$<br>$r(t) = \sin^3 t + \cos^3 t$ |  | higher order polynomial |

SYSTEM AND METHOD TO ESTIMATE REGION OF TISSUE ACTIVATION

CROSS-REFERENCE TO RELATED APPLICATIONS

This application is a continuation of U.S. patent application Ser. No. 16/431,581, filed Jun. 4, 2019, which is a continuation of U.S. patent application Ser. No. 13/839,906, filed Mar. 15, 2013, which issued as U.S. Pat. No. 10,360,511, which is a continuation of U.S. patent application Ser. No. 12/869,159, filed Aug. 26, 2010, which issued as U.S. Pat. No. 8,589,316, which claims the benefit of U.S. Prov. Pat. App. Ser. No. 61/237,375, filed Aug. 27, 2009, the entire contents of each of which is incorporated by reference herein. The entire contents of each of U.S. patent application Ser. No. 13/480,858, filed May 25, 2012, U.S. patent application Ser. No. 11/606,260, filed Nov. 28, 2006, U.S. Prov. Pat. App. Ser. No. 60/740,031, filed Nov. 28, 2005, U.S. Prov. Pat. App. Ser. No. 61/120,006, filed Dec. 4, 2008, and U.S. patent application Ser. No. 10/885,982, filed Jul. 7, 2004, which issued as U.S. Pat. No. 7,346,382, are also incorporated by reference herein.

GOVERNMENT FUNDING

This invention was made with government support under Grant No. NIH R01 NS059736. The U.S. government has certain rights in the invention.

TECHNICAL FIELD

The present invention relates generally to systems and methods for estimating a region of tissue activation, such as for stimulation in a patient's brain or spinal cord.

BACKGROUND

Electrical stimulation of the nervous system has provided a therapeutic treatment for a variety of disorders. For example, electrical stimulation has been applied to pain management, such as by performing stimulation of the spinal cord. Electrical stimulation has also been performed to augment hearing in the context of cochlear implants. Deep brain stimulation (DBS) has become an established therapy for treating various conditions including, for example, Parkinson's disease and dystonia. DBS has also been employed to treat several other conditions, such as clinical depression, obsessive compulsive disorder, and epilepsy to name a few.

By way of further example, the discovery that high frequency DBS generates clinical benefits analogous to those achieved by surgical lesioning has transformed the use of functional neurosurgery for the treatment of movement disorders. In first world countries, thalamic DBS for intractable tremor has replaced ablative lesions of the thalamus, and DBS of the subthalamic nucleus or globus pallidus internus (GPi). GPi has replaced pallidotomy in the treatment of the cardinal motor features of Parkinson's disease (e.g., tremor, rigidity, bradykinesia). In addition, GPi DBS has emerged as an effective therapy for dystonia, and the utility of DBS is being examined for the treatment of epilepsy, obsessive-compulsive disorder, Tourette's syndrome, and major depression.

Despite the documented clinical successes of neurostimulation, the mechanisms and effects of neurostimulation at the neuronal level remain difficult to predict. As a result, modeling and simulation have played increasingly important roles in the engineering design and scientific analysis of neurostimulation.

SUMMARY

The invention relates generally to systems and methods for estimating a region of tissue activation, such as associated with stimulation in a patient's neural tissue (e.g., brain or spinal cord).

In one embodiment, an artificial neural network (ANN) is programmed to output parameters of a mathematical expression that corresponds to an estimated volume of tissue activation (VTA) for a set of input parameters (electrode configuration, stimulation parameters). A given ANN can determine the estimated VTA for different for electrode configurations and stimulation parameters for which no simulations or clinical studies have been performed. Additionally, the ANN can be trained to provide the estimated VTA for a plurality of different types of electrodes without requiring retraining of the ANN for the different types of electrodes.

In another embodiment, the present invention provides a computer-implemented method for determining the volume of activation of neural tissue, comprising: (a) having one or more parametric equations that define a volume of activation, wherein the parameters for the one or more parametric equations are given as a function of an input vector that includes stimulation parameters; (b) receiving input data that includes values for the stimulation parameters and defining the input vector using the input data; (c) applying the input vector to the function and obtaining the parameters for the one or more parametric equations; and (d) solving the parametric equation to calculate the volume of activation. The calculated volume of activation may be displayed on a display screen.

In another embodiment, the present invention provides a method for determining a function that outputs the parameters of one or more parametric equations that define a volume of activation, comprising: (a) having an electric field model of an electrode and a neural tissue model; (b) coupling the electric field model to the neural tissue model to obtain volumes of activation for multiple different sets of stimulation parameters and electrode configuration parameters; (c) fitting a geometric shape to the volumes of activation, wherein the geometric shape is defined by one or more parametric equations; and using a computational training algorithm to design a function that correlates the different sets of stimulation parameters and electrode configuration parameters to the parameters for the one or more parametric equations that represent the geometric shapes that are fitted to the volumes of activation. In another embodiment, the present invention provides a non-transitory computer-readable storage medium comprising instructions for determining the volume of activation using one or more parametric equations whose parameters are given as a function of an input vector that includes stimulation parameters and electrode configuration parameters, wherein the function is obtained by this method.

DETAILED DESCRIPTION

Figure 1:
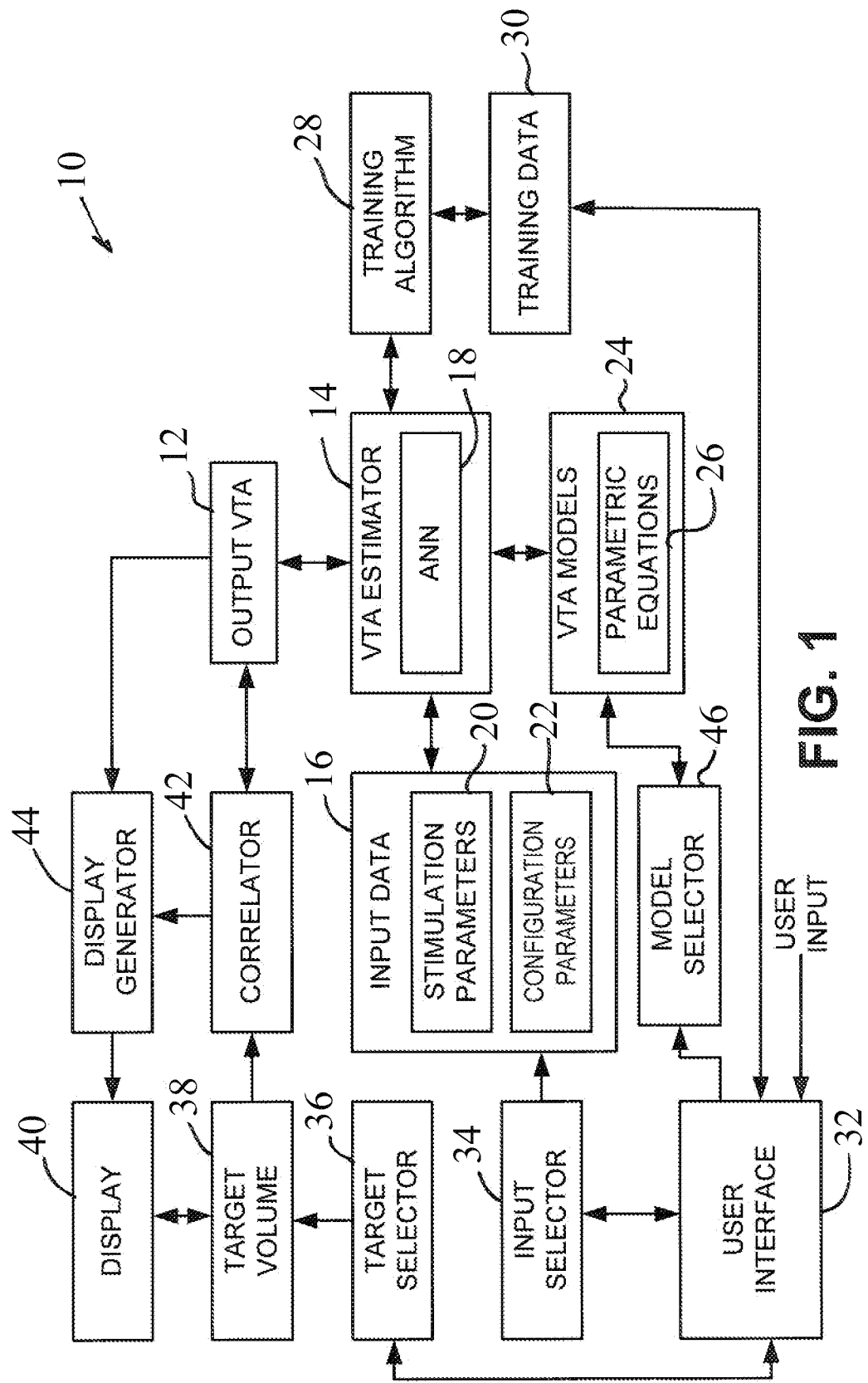
FIG. 1 depicts a functional block diagram of an example approach that can be employed to determine a volume of tissue activation according to an aspect of the invention.

The invention relates generally to systems and methods for estimating or predicting a volume of neural tissue (for example, in the brain or spinal cord) activated by electrical stimulation. FIG. 1 depicts an example of a system 10 that can be implemented to estimate a volume of neural tissue activated, indicated as an output volume of tissue activation (VTA) 12. The system 10 includes a VTA estimator 14 that is programmed to provide the output VTA for a set of input data 16. The VTA estimator 14 can employ artificial intelligence and/or machine learning techniques (e.g., artificial neural networks, function predictors, expert systems or the like).

In the example of FIG. 1, the artificial intelligence component of the VTA estimator 14 is depicted as being artificial neural network (ANN), although it would be understood and appreciated other techniques and methodologies could be utilized based on teachings herein. The ANN 18 is trained to provide the output VTA 12 in response to the input data 16 according to the complex relationships between the input data 16 described or modeled by the ANN 18.

The input data 16 includes stimulation parameters 20 and configuration parameters 22. Collectively the stimulation parameters 20 and configuration parameters 22 can define an input vector, based on which the output VTA 12 is to be calculated. It will be understood and appreciated that the particular number of dimensions for the input vector can vary according to application requirements and capabilities of a corresponding ANN 18. The input stimulation parameters 20, for example, can include an indication whether the stimulation is activated by voltage or current control device. The input data 16 can also include stimulation parameters 20, such as voltage or current amplitude, frequency, pulse width and pulse shape.

The electrode configuration parameters 22 can define structural characteristics, such as dimensions and configurations and interrelationships for an electrode design. The configuration can be set for commercially available electrode designs or to a custom design. For the example of an electrode having a plurality of cylindrical electrode contacts, the electrode configuration parameters 22 can include the height, diameter and spacing (or distribution) of the electrode contacts along the electrode shaft. Relationships between parameters can also be represented in the input data 16, such as the aspect ratio (d/h). The aspect ratio further can be utilized to constrain the optimization procedure, such as by limiting the search space to a predefined range of aspect ratios (e.g., d/h<some predefined value).

Additionally, the stimulation parameters 20 and the configuration parameters 22 can be interrelated. For instance, a given configuration of electrode can have any number of one or more electrode contacts, corresponding stimulation parameters 20 may thus be provided for stimulation of the one or more electrode contacts. Additionally, the stimulation parameters can define whether a given contact is an anode or cathode. It will be appreciated that a given set of input data (e.g., stimulation and configuration parameters) corresponds to a given output VTA 12. Thus there can be any number of input data 16, which can be varied to provide corresponding output VTAs, as described herein.

The ANN 18 can employ VTA models 24 to mathematically represent or describe a region, which can be an area (e.g., in two dimensions) or volume (e.g., in three dimensions) for the activated region of tissue represented in the output VTA 12. Thus the VTA models 24 can include a set of one or more parametric equations 26 which can be utilized individually or in any combination thereof in the ANN 18 for use in computing the output VTA 12 based on the input data 16.

Figure 2:
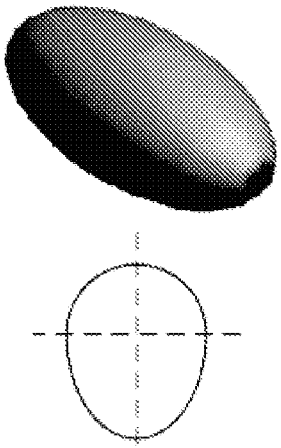
FIG. 2 depicts an example of models that can be utilized to describe a region of tissue activated.
Figure 2:
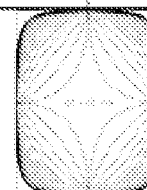
Figure 2:
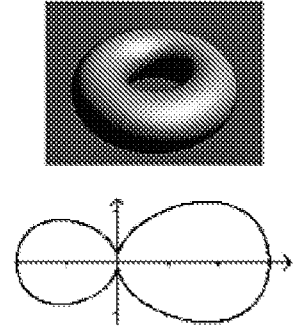

FIG. 2 depicts examples of some parametric equations 26 that can be utilized by the VTA estimator 14. In the example of FIG. 2, parametric equations are illustrated for an ellipsoid, a super ellipsoid as well as for higher order polynomials. It will be understood and appreciated other shapes and parametric equations and combinations thereof can be utilized as VTA models 24. In the example equations in FIG. 2, A and B are the equatorial radii (along the x and y axis, respectively) and C is the polar radius along the Z axis. The parameters r and t with respect to parametric equations control the amount of flattening at the tips at the equator.

It will be understood and appreciated that the center of each geometric volume described by the parametric equations 26 can represent an active region which may or may not be at the center of the active contacts in the electrodes being modeled thereby. The particular center of the contacts and the center of the active regions may differ depending on, for example, the stimulation and configuration parameters (e.g., the contact configuration on the voltage, electrode type pulse width, impedance or other stimulation or configuration parameters) 20 and 22, respectively.

The VTA estimator 14 can utilize any number of one or more artificial neural networks (ANN) 18. By further example, the VTA estimator 14 can estimate the parameters of the mathematical parameters for the parametrical equations 26 defining the volumes of neural tissue activated without having to perform neuronal model simulations or refit equations to a given activation spread.

Figure 3:
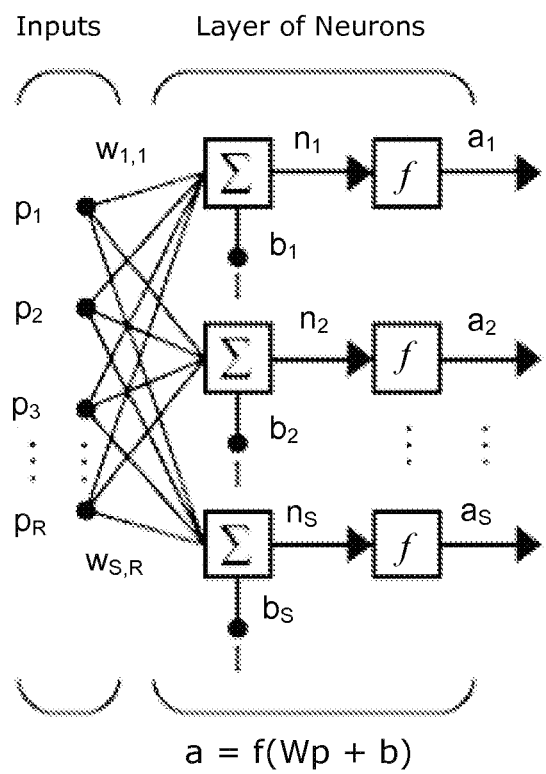
FIG. 3 depicts an example of an artificial neural network that can be implemented.

As a further example, the VTA estimator 14 can employ one or more artificial neural networks, such as two-layer neural networks depicted in FIG. 3 (see, e.g., Mathworks Neural Network Toolbox, www.mathworks.com/access/helpdesk/help/pdf_doc/nnet/nnet.pdf), to create VTA predictors programmed to estimate the parameters of the mathematical equation(s) 26 defining the volumes of neural tissue activated. Advantageously, the estimation can be implemented without having to perform neuronal model simulations or refit the equations to the activation spread. As one example case where VTAs are modeled with ellipsoids, the VTA estimator 14 can be implemented with a pair of two-layer neural networks with sigmoid and linear transfer functions in the hidden and output layers, respectively.

Examples of sigmoid transfer function that can be utilized in the layers of the ANN 18 are described in Narendra K. S., Parthasarathy K. (March 1991) "Gradient methods for the optimization of dynamical systems containing neural networks," IEEE Transactions on Neural Networks, Vol. 2, No. 2, 252-262. Examples of linear transfer function that can be utilized in the layers of the ANN 18 are described Jonic S., Jankovic T., Gajic V., Popovic D. (March 1999) "Three machine learning techniques for automatic determination of rules to control locomotion," IEEE Trans. On Biomedical Engineering, Vol. 46, No. 3, 300-310.

Continuing with the example of two ANNs 18, one ANN can contain 12 inputs (e.g. representing pulsewidth, impedance, configuration number, voltage amplitude, contact configuration, active ellipsoids), 20 hidden neurons, and 8 output neurons (a0, c0, a1, c1, a2, c2, a3, c3) that define the ellipsoid parameters (b=a due to axi-symmetric properties of model). The architecture of the second ANN 18 can be the same as the first, but the outputs were the centers of up to four VTAs or active regions along the vertical axis of the electrode shaft (z0, z1, z2, z3). Those skilled in the art will understand and appreciate various types of transfer functions (other than the sigmoidal and linear functions described above) and any numbers of layers that can be utilized to implement the ANN 18.

The ANN 18 can be pre-trained on the system 10 such with a set of training data 30 so that the ANN is valid for generating the output VTA 12 over a range of the input parameters 16. The system 10 can also be trained for a given application or retrained in the event that a user wishes to expand the range of the VTA estimator to accommodate additional input data outside the range of the original training of the ANN 18.

The system 10 can include a training algorithm 28 that can retrain the ANN 18 based on the set of training data 30. The training data 30 can be pre-processed or normalized to provide a normalized set of training data 32 according to the requirements of the ANN 18. For instance, the training data 30 can be obtained using computer simulations of axonal cable models.

The training algorithm 28 can implement back propagation or propagation of error based on applying the training data 30 to desired output data using the ANN 18. As one example, each ANN 18 can be trained (or retrained) using the Levenberg-Marquardt and the gradient decent with momentum algorithm.

Examples of possible training algorithms according to these methods are disclosed in the following: Gill P. R., Murray W., Wright M. H. (1981) "The Levenberg-Marquardt Method" in Practical Optimization. London: Academic Press, 136-137; Levenberg K. (1944) "A Method for the Solution of Certain Problems in Least Squares" Quart. Appl. Math. Vol. 2, 164-168; and Marquardt D. (1963) "An Algorithm for Least-Squares Estimation of Nonlinear Parameters" SIAM J. Appl. Math. Vol. 11, 431-441.

As an example for initial training, some or all of the available input/output data corresponding to actual stimulation cases, which has been utilized to determine VTAs, can be utilized to train the VTA estimator 14. A subset of the available cases can be used as validation data to avoid over-fitting, and yet another subset or the remaining cases can be utilized to estimate the generalization error. The neural network weights and biases can be initialized randomly. Each ANN 18 can be trained until the normalized fitting mean squared error (MSE) reached a predetermined value (e.g., less than 1e-5), until the validation error increased with respect to the fitting error, or for a maximum of number (e.g., 1000) of epochs.

After the VTA estimator 14 has been programmed such as by training the ANN 18, the system 10 can then be utilized to generate output VTA 12 for a set of the input data 16. To facilitate such process, the system 10 can include a user interface 32 which can include a variety of buttons, drop down menus or other graphical and text based user interface elements, as is known in the art. The user interface 32, for example, can be utilized to provide or access a set of input data 16 or otherwise define a method of operation or mode of operation to be implemented by the system 10.

The generalized relationships between the input data vector 16 and output VTA 12 is achieved through trained artificial neural networks. To calculate the parameters of the mathematical equation(s) that define a VTA, a series of simple equations can be solved. As one example, the equations can have the following form:

$$I_H = \frac{2I - \max(I_T) - \min(I_t)}{\max(I_T) - \min(I_t)}$$

$$HL = IW \cdot I_H + b_1$$

$$o_1 = \frac{1}{1 + e^{-HL}}$$

$$o_2 = LW \cdot o_1 + b_2$$

$$\text{output} = \frac{o_2[\max(T_T) - \min(T_T)] + \max(T_T) + \min(T_T)}{2}$$

Where n is the number of hidden neurons;

m is the number of network outputs;

I is the 12×1 input vector for which we want to calculate the VTA;

$\max(I_T)$ and $\min(I_T)$ define the maximum and minimum values, respectively, that the inputs can achieve;

IW are the n×12 input weights;

b1 is the n×1 input bias vector;

o1 is a n×1 vector that contains the output from the input layer. LW and b2 are the m×n matrix of weights and m×1 vector of biases, respectively, for the hidden layer;

o2 is the m×1 normalized output vector;

$\max(T_T)$ and $\min(T_T)$ are the m×1 vectors that define the maximum and minimum values, respectively, that the outputs can achieve; and output is the m×1 vector of parameters that define the VTA.

Referring back to FIG. 1, the system 10 can also include a model selector 46 that is operative to select one or more VTA models 24. The model selector 46 can be implemented manually, such as in response to user input received via the user interface 32. Alternatively, the model selector 46 can be implemented as an automatic process that is programmed to select an appropriate one or more of the parametric equations based on the input data. For instance, the model selector 46 can employ a constrained optimization algorithm to minimize a cost function formed by multiple (e.g., three) components and ensure maximum fit between the parametric equations 26 and the spread of fiber activation corresponding to the VTA. As a further example, a first cost function component can correspond to the difference between the most distal edges (on both the horizontal and vertical planes) of our parametric equation and the 2D contour. A second component can correspond to the perimeter-length difference between the area covered by the parametric equation and the 2D contours. A third component can correspond to the difference in area covered by the parametric equation and by the 2D active fiber contour.

In one example embodiment, a constrained optimization on the data can be performed using the Matlab® Optimization Toolbox's function function (The MathWorks Inc., Natick, Mass.), although other commercially available or proprietary methods can be utilized. This optimization method finds a minimum of a constrained nonlinear multi-variable function using Sequential Quadratic Programming (SQP) [Coleman and Zhang 2006]. SQP is described in detail in the following: Powell M. J. D., (1983) "Variable Metric Methods for Constrained Optimization," Mathematical Programming: The State of the Art, (A. Bachem, M. Grotschel and B. Korte, eds.) Springer Verlag, 288-311; Fletcher R., (1987) "Practical Methods of Optimization," John Wiley and Sons; Gill P. R., Murray W., Wright M. H. (1981) "The Levenberg-Marquardt Method" in Practical Optimization. London: Academic Press, 136-137; and Hock W., Schittkowski K., (1983) "A Comparative Performance Evaluation of 27 Nonlinear Programming Codes," Computing, Vol. 30, 335. Those skilled in the art will understand and appreciate other commercially available and proprietary tools and software that can be utilized for selection of appropriate parametric equations 26.

Each active area thus can be described by one of the parametric equations (e.g., ellipsoids, super ellipsoids, second or higher order polynomials, etc.) or combination of any two or more parametric equations, such as shown in FIG. 2. While three parametric equations are depicted in FIG. 2, those skilled in the art will appreciate that other numbers and shapes can be utilized as parametric equations.

By way of further example, the user interface can invoke an input selector 34 to define one or more set of input data 16, such as including the stimulation parameters and/or the configuration parameters 20 and 22. Alternatively, the input selector 34 can be utilized to select an input mode, such as to set the system for determining a set of input data that can be utilized to provide a desired target VTA. The system 10 can also include a target selector 36 that is utilized to define and/or set a desired target volume of tissue to be activated 38. The target volume 38 can be selected via the user interface, such as corresponding to a 2-D and/or 3-D representation, which may be presented on a corresponding display 40. For example, the display 40 can provide a three dimensional or two dimensional representation of an anatomical region such as the brain in which the target volume resides. The 3-D model presented on the display can correspond to a general model of brain anatomy. Alternatively, the model represented on the display 40 can correspond to a patient-specific model, such as can be generated using a corresponding imaging modality (e.g., CT scan or MRI or the like).

Where a target volume 38 has been selected via the target selector 36, the system 10 can employ a correlator 42 that is programmed to perform mathematical correlation between the target volume and the output VTA 12. The correlator 42 can perform correlation between the output VTA 12 and the target volume 38 to calculate a volume or area of overlap between the output VTA and the model volume represented by the target VTA. As one example, the correlator 42 can be programmed to perform a constrained optimization algorithm. The corresponding results can be sent to a display generator 44 and in turn reproduced for visual presentation (and comparison) on the display 40.

Where the system 10 is being utilized to determine a set of input data 16 to achieve a corresponding target volume 38 that has been selected, the input selector 34 can vary the stimulation and/or configuration parameters 20 and 22 over a range of available settings. Each corresponding output VTA can be correlated by the correlator 42 relative to the target volume 38 and provided a score indicative of the amount of overlap. The VTAs 12 and 38 and their scores can be displayed to a user, such as by providing corresponding data to the display 40 or other output device (e.g., a printer). The output VTA having a maximum amount of overlap relative to the target volume can be determined and the corresponding input data provided as an output on the display or to another output device (not shown).

The given set of input data thus can represent a particular structure for an electrode as well as stimulation parameters, which can be utilized to achieve the desired target VTA. The system 10 may also provide a graphical representation on the display 40 of an electrode design corresponding to the configuration parameters 22 for the output VTA. The electrode design can be a commercially available design or a custom design. It will be appreciated that there can be more than one target VTA and thus more than set of input data for a given patient.

It will be further appreciated that for each of the different sets of input data (e.g., including stimulation parameters and configuration parameters) the trained ANN 18 can be utilized for rapid evaluation of the respective designs to ascertain design and stimulation parameters without having to retrain or perform additional simulations for clinical measurements. Accordingly, those skilled in the art will understand and appreciate that the system 10 and the VTA estimator 14 can be utilized to assist the interoperative planning of electrode tracks or deep brain stimulation (DBS) or other stereotactic surgery by helping to identify an implant location for the DBS electrodes. This could be utilized by adjusting the target volume with respect to an accordance system in the user and determining the output VTA 12 at each respective location and for different simulation parameters until a best match is found.

The system 10 can also include one or more other input or output devices (not shown). Such devices can provide an interface through which a user can input data as well as control the methods. For example, a user can employ the I/O device to input data, such as instructions to initiate or modify the electrode design procedure. Alternatively, the I/O device can be employed to acquire the training data 30, such as from a location in local memory, from another storage location, or to access another process running on another computer.

EXPERIMENTAL

The following discussion relates to activities of the inventors that include experiments and procedures that provide a foundation for the concepts described herein, including procedures used for determining parametric equations and VTAs for training data suitable for use in an ANN.

Figure 8:
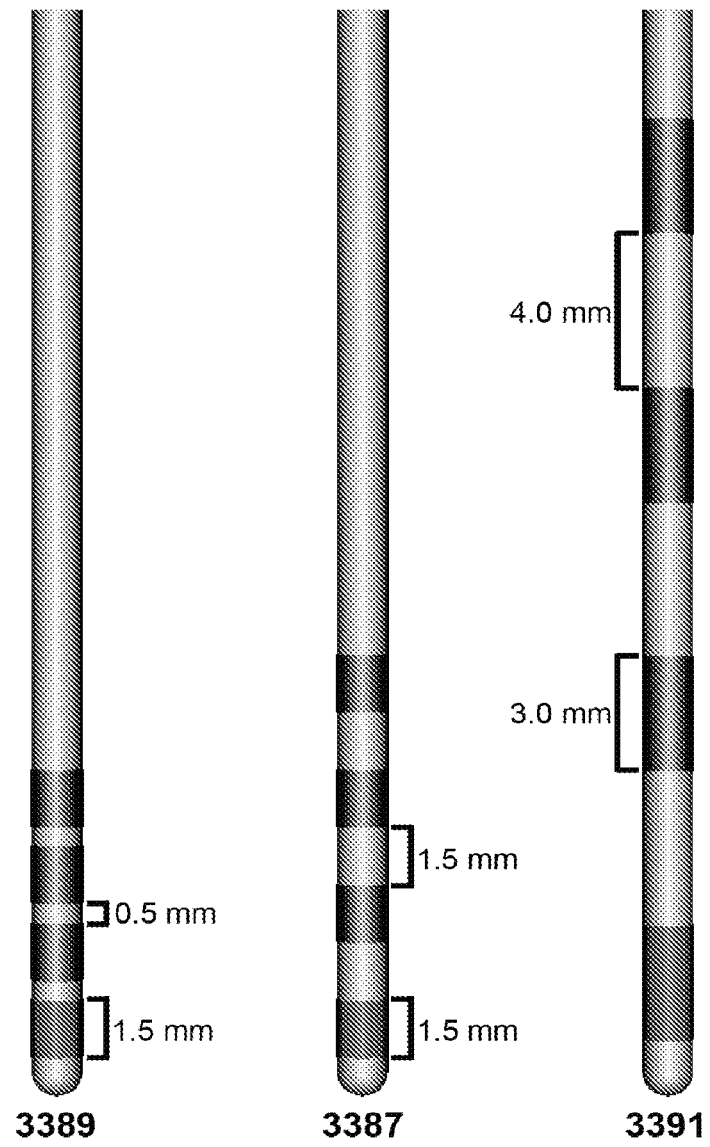
FIG. 8 depicts the electrode configuration for three Medtronic electrodes used in the computational trials.

A computational model of deep brain stimulation was created to estimate the spatial spread of neural activation within the brain and characterize the volumes of tissue activated. This computational of deep brain stimulation had both anatomical and electrical components. The electrical components included three virtual electrodes created from geometric representations of Medtronic deep brain stimulation electrodes (model numbers 3389, 3387, and 3391; Medtronic, Minneapolis, Minn.), as shown in FIG. 8.

Electric Field Model

The computational modeling studies included a model of a virtual electrode inserted inside brain tissue. The virtual electrodes were modeled to represent Medtronic 3389, 3387, and 3391 deep brain stimulation electrodes (see FIG. 8). For each virtual electrode, over 150 axi-symmetric, multi-resolution, finite element models (FEM) were created to model the electric field within the brain tissue. The FEMs were created using COMSOL (Comsol Inc., Burlington, Mass.) and SCIRun 3.3 (Scientific Computing and Imaging Institute, Salt Lake City, Utah), and included representations of the virtual electrode, the electrical conductivity of brain tissue surrounding the electrode, capacitance at the electrode-tissue interface, a thin layer of encapsulation tissue around the electrode, and stimulation settings typically used in clinical applications.

The electrodes were represented as purely capacitive elements with a 3.3 µF (for the Medtronic 3387 and 3389 electrodes) or 6.6 µF (for the Medtronic 3391 electrode) capacitance to reflect the contact size. The brain tissue was represented as a homogeneous, isotropic medium having a bulk conductivity of 0.3 S/m. The model also incorporated a 0.5 mm thick encapsulation layer surrounding the electrode to account for charge transduction reactions and a 42% voltage drop at the electrode-tissue interface. The conductivity of the encapsulation layer in each model was adjusted to match the target impedance. A range of stimulation settings and electrode configurations (see Table 1 below) were applied to the electric field model and a Fourier FEM solver was used to solve Poisson's equation with Dirichlet and Neumann boundary conditions. The ground conditions of the electric field model were the boundaries of the FEM mesh if there were no anodes present during stimulation, or the anode(s) if they were present.

TABLE 1

| | |
|---|---|
| Electrodes: | 3389, 3387, 3391 |
| Frequency: | 130 Hz |
| Pulse-widths: | 60, 90, 120, 150, 180, 210, 450 µs |
| Amplitudes: | 1, 2, 3, 4, 5, 6, 7, 8, 9, 10 V |
| Impedances: | 0-749, 750-1250, 1251 + Ω |
| Contact configurations: | 15 monopolar, 12 bipolar, 28 tripolar, 10 quadripolar |

Neural Tissue Model

Figure 4:
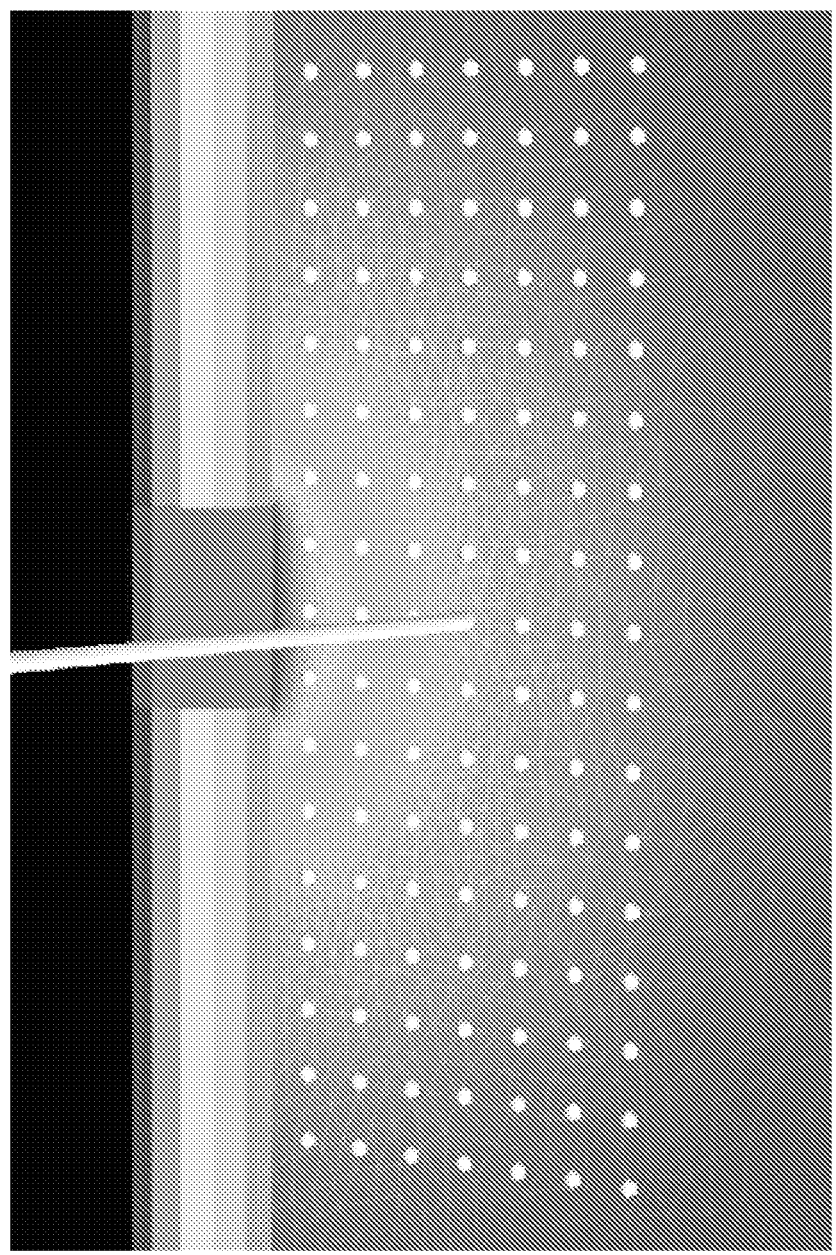
FIG. 4 depicts an example of an axon model and electrode structure that can be utilized to identify a region of tissue activated.
Figure 9:
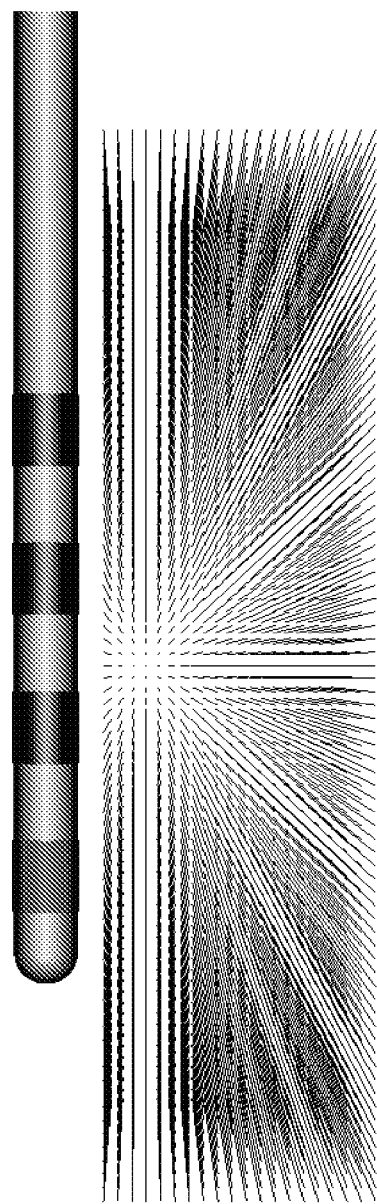
FIG. 9 depicts a Medtronic 3387 electrode in an axi-symmetric finite element model with the axon fibers oriented perpendicular to the electrode shaft.

The electric field model was coupled to a neural tissue model to determine neuronal activation. As shown in FIG. 9, the neural tissue model had over 2,500 trajectories of white matter axon fibers which were distributed in a matrix perpendicular to the electrode shaft with an inter-fiber resolution of 0.2 mm along the vertical (dorsal-ventral) and horizontal (medial-lateral) axes. The axon population was positioned about 0.7 to 11.0 mm lateral to the electrode shaft, and −7.0 to +32.0 mm above the tip of the electrode. FIG. 4 shows another illustration of how the axons can be arranged in a matrix adjacent the electrode shaft. A multi-compartment model of a myelinated axon was created to represent each of these axons. Axonal parameters for these models were defined according to McIntyre et al. for 5.7 µm axons (McIntyre et al., J Neurophysiol. 2002 February; 87(2):995-1006). The geometry required to explicitly define the trajectory of each axon was determined using Matlab (Mathworks Inc., Natick, Mass.). Because of the perpendicular orientation of the axons, the spread of activation relative to the electrode shaft could be determined.

The extracellular voltages along each axon model was determined by interpolating each electric field onto each axon compartment. The axonal behavior in response to extracellular stimulation was simulated for all axon models and each of the electric field FEMs using the NEURON simulator. In this simulation, an axon was considered activated if it fired an action potential in response to the applied electric field simulation.

The activated fibers were grouped into active regions. For simplicity, active regions for each active electrode contact (cathode or anode) on the virtual electrode were defined. Each activated fiber was assigned to the nearest active region by its distance from the center of each fiber to the center of each electrode contact. Each active region could have more than one contact, but a given contact could only belong to a single active region. As such, each active region was defined as either cathodic or anodic, depending on the nature of its corresponding electrode contact. If an activated fiber was equidistant to a cathode and an anode, the fiber was considered to be activated by the cathode. In some cases, adjacent active regions were merged into a single active region depending upon the electrode configuration and symmetry.

Figure 6:
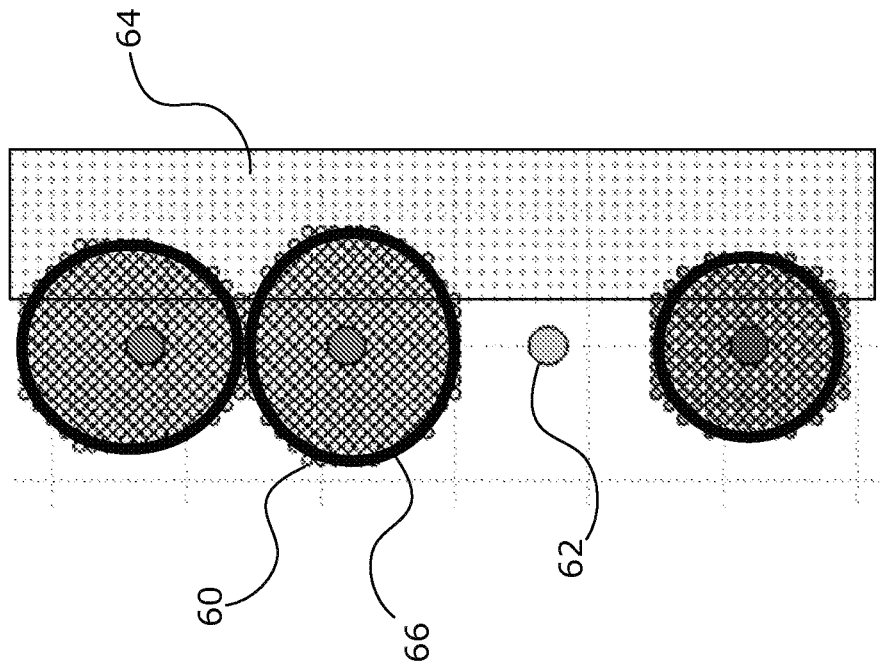
FIG. 6 depicts an example of a region of tissue activated for a second set of stimulation parameters and configuration parameters.
Figure 5:
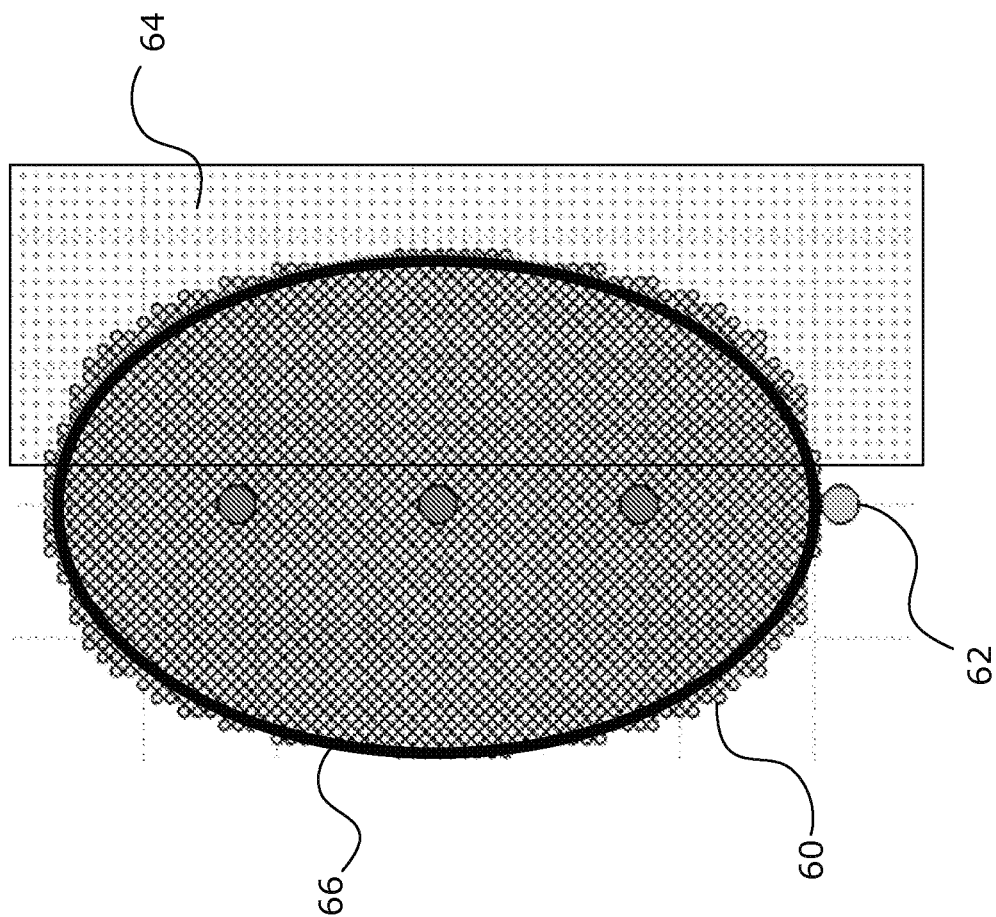
FIG. 5 depicts an example of a region of tissue activated for a first set of stimulation parameters and configuration parameters.
Figure 11:
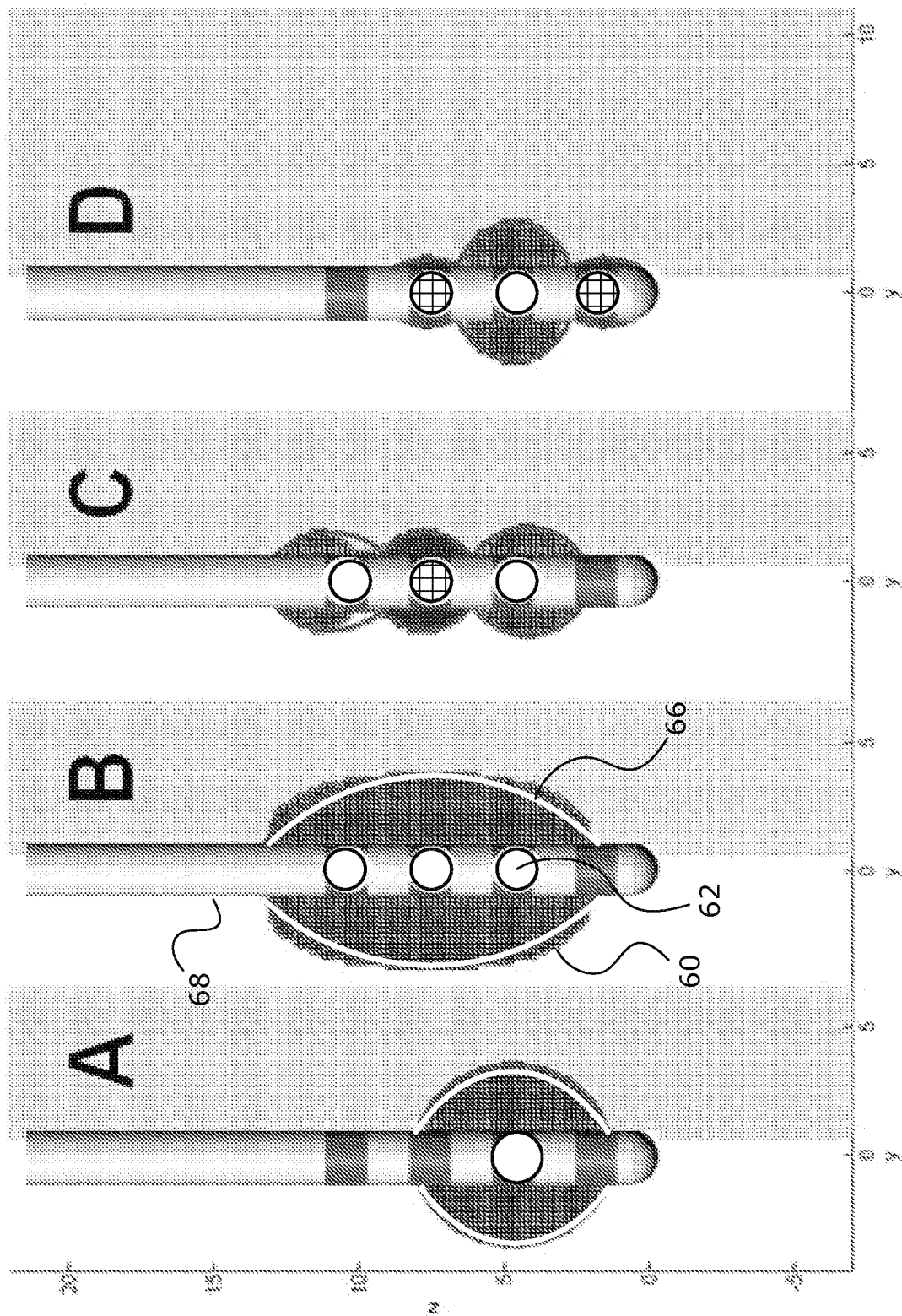
FIG. 11 depicts an example of regions of tissue activated by different configurations for electrode contact activation.

The two-dimensional boundaries of each active region were defined by a parametric equation for an ellipse that best encompassed the spread of activated fibers within its horizontal and vertical planes. A constrained optimization algorithm was used to find the parameters of this parametric equation that minimized the root mean squared (RMS) error between the actual boundaries of the active region and the geometric outline defined by the parametric equation. The upper and lower bounds were defined by obtaining the maximum lateral and vertical distances from each active fiber to the center of the active region. Because this was an axi-symmetric stimulation model, the 2D elliptical outline generated by the parametric equation could be rotated around the electrode shaft (z-axis) to create a three-dimensional VTA. FIGS. 5 and 6 depict examples of active regions 60 that can be determined by measuring the spread of the fibers 64 in each active region 60. The elliptical outline 66 of each active region 60 are 2D contours on a plane parallel to the electrode contacts 62 and centered on the electrode shaft. The edges 66 define an ellipse that has been optimally fitted to its respective active region 60. FIG. 11 shows another example of active regions 60 under different configurations for electrode contact activation. The elliptical outlines 66 of the parametric equation fitted to the active regions 60 are shown as a white lines around active regions 60. On the electrodes 68, active contacts 62 that are cathodes are shown as blank circles and those that are anodes are shown as cross-hatched circles.

Once the spatial spread of activation was quantified for every stimulation setting through a set of parameters describing each 2D outline/shape, artificial neural networks were used to model the complex relationships between the electrode parameters (stimulation settings and configurations) and the optimally fit ellipsoid shape that represents the volume of activation. Two feed-forward artificial neural networks (ANNs) were trained using the activation spreads and the associated set of electrode parameters as the training data.

The ANNs were used to design a predictor function of the form $P=wI+b$, which linearized the complex non-linear relationships between stimulation settings (I) and the equation parameters (P) describing the 3D tissue activation, where w and b represent the weights and biases, respectively. The ANN finds the set of weights and biases mapping these inputs to their corresponding outputs. The first ANN was used to calculate the vertical and lateral spread of activation for each active region. The second ANN was used to calculate the vertical center of each active region. Because the model was axi-symmetric, the 2D boundaries of activation could be swept along the major axis of the virtual electrode to generate 3D volumes of tissue activated. Use of the ANNs allowed interpolation between stimulation settings that were not explicitly analyzed through the FEM solutions and NEURON simulations. This allowed selection of any stimulation setting within the parameter space to generate a 3D VTA within the brain.

Each artificial neural network was created using MATLAB's neural network toolbox (Mathworks Inc., Natick, Mass.). Each network received 12 inputs: stimulation parameter set, pulse-width, encapsulation conductivity, contact configuration, voltage amplitude, and Boolean flags (1=active, 0=inactive) describing the electrode configuration (i.e., active contacts). Each ANN also included one hidden layer with 20 neurons using a sigmoid transfer function and a linear output layer. The first neural network had eight outputs (radial and vertical spread of simulation for each active region) and the second neural network had four outputs (ellipsoid center along the electrode shaft for each active region).

Both neural networks were trained using the Levenberg-Marquardt algorithm on a random sampling of 70% of the stimulation settings and their corresponding ellipsoid parameters. The remaining 30% of the data were used for validation and assessing the performance of the neural networks. The initial weights of each ANN were initialized randomly, and the stopping criteria used to terminate training included a mean squared error less than $10^{-5}$ or up to 500 epochs.

With the predictor function, it is possible to calculate the ellipse equation parameters that defined the volume of tissue activation for a wide range of multipolar electrode configurations and stimulation settings. The input (I) consisted of 12 values:

$$I = [PW, \sigma_{encap}, n, V, c_0, c_1, c_2, c_3, e_0, e_1, e_2, e_3],$$

where PW is the pulse-width, $\sigma_{encap}$ is the conductivity of the tissue encapsulation layer surrounding the electrode (dynamically based on patient-specific impedance values), n is the configuration number for the specific stimulation settings, V is the voltage amplitude, $C_{0-3}$ are the explicit contact configurations (0 if dormant, $-1$ if cathode, and $+1$ if anode), and $e_{0-3}$ are the active ellipsoids generated based upon the active contact configurations using a pseudo-algorithm as follows: * Set $e_{0-3}$ to 1 if the corresponding $C_{0-3}$ contacts are active; * If there are no anodes in contacts $C_{0-3}$, then determine if there are adjacent cathodes; * If there are adjacent cathodes, then set 1 to the active $e_{0-3}$ corresponding to the lowest adjacent cathode contact(s) and 0 to the active $e_{0-3}$ corresponding to the higher adjacent cathode contact(s). This pseudo-algorithm demonstrates an example of how adjacent active regions can be combined if any overlap is present.

The ellipse parameters were solved using weights and biases calculated for each electrode type by the artificial neural networks. The inputs of the ANN were normalized to the range ±1 prior to calculation of the outputs. The normalized inputs ($I_{norm}$) were defined by:

$$I_{norm} = \frac{2 \times I - I_{max} - I_{min}}{I_{max} - I_{min}},$$

where $I_{max}$ and $I_{min}$ are matrices containing the extreme maximum and minimum values of each input parameter, respectively.

The calculation of the normalized output ($O_{norm}$) was performed using the generalized sigmoid-based equation:

$$O_{norm} = \frac{W_{layer}}{1 + e^{-(W_{input} \times I_{norm} + b_{input})}} + b_{layer},$$

where $W_{layer}$ and $W_{input}$ are the layer and input weights, respectively, and $b_{layer}$ and $b_{input}$ are the layer and input biases, respectively. The final output (O) was defined as:

$$O = \frac{O_{norm} \times (T_{max} - T_{min}) + T_{max} + T_{min}}{2},$$

where $T_{max}$ and $T_{min}$ are matrices containing the extreme maximum and minimum values of each output parameter, respectively. The output was an 8×1 (network 1) or 4×1 (network 2) matrix containing the parameters for the parametric equation. For example, in the case of the equation for an ellipsoid of the form $x^2/a^2 + y^2/b^2 + z^2/c^2 = 1$, the a and c parameters for each active ellipse, and the z center of each active ellipse, respectively. The VTAs were visualized in 3D along with their appropriate virtual electrode using the SCIRun/BioPSE visualization environment.

In certain embodiments, the present invention provides a computer-implemented method for determining the volume of activation of neural tissue. The method uses one or more parametric equations that define a volume of activation. The parameters of the parametric equations are given as a function of an input vector. As explained above, the input vector may include stimulation parameters and/or electrode configuration parameters. Also as explained above, examples of such stimulation parameters include voltage or current amplitude, frequency, pulse width, and pulse shape. Also as explained above, the electrode configuration parameters can define structural characteristics of the electrode, such as its dimensions (e.g., height and diameter of the electrode contacts) or the spacing or distribution of the electrode contacts. Also as explained above, the parametric equations may represent various geometric shapes, such as ellipsoid shapes (including super-ellipsoid shapes). In some cases, the function defining the parameters of the parametric equation may be a linear function of the input vector. In other cases, the function defining the parameters of the parametric equation may be a non-linear function of the input vector.

The desired stimulation parameters and/or electrode configuration parameters are received as input data. The values in the input data are used to define the input vector for the function. For example, the input data may include values for pulse width, encapsulation tissue conductivity, voltage, and electrode contact configuration, and these values are used to define the corresponding variables in the input vector. The output of the function can then be calculated, which is then used to define the parameters of the parametric equation. For example, in the case of a parametric equation for an ellipse ($x^2/a^2 + y^2/b^2 + z^2/c^2 = 1$), the output of the function can define the parameters of the ellipse. This parametric equation can then be solved for the volume of activation as an ellipsoid shape. Thus, this method allows for the volume of activation to be calculated directly from the solution to the parametric equation.

As explained above, the parametric equation used to calculate the volume of activation can be obtained using a computational training algorithm, such as an artificial neural network. In particular, the computational training algorithm can be used to design a function that correlates different stimulation parameters and/or electrode configuration parameters to the volumes of activations (i.e., the training data set) produced by the different stimulation parameters and/or electrode configuration parameters.

This training data set can be obtained by coupling an electric field model to a neural tissue model to obtain volumes of activation for multiple different sets of stimulation parameters and/or configurations. Examples of how an electric field model can be coupled to a neural tissue model to calculate a volume of activation are described in U.S. Pat. No. 7,346,382 (McIntyre et al.), U.S. Patent Application Publication No. 2007/0288064 (Butson et al.), and U.S. Patent Application Publication No. 2009/0287271 (Blum et al.), which are all incorporated by reference herein.

As explained above, in some cases, these volumes of activation can be fit to a geometric shape defined by a parametric equation. Also as explained above, this fitting of the volume of activation can be performed using an optimization algorithm. Thus, with this information, the training set may include multiple different sets of electrode parameters (stimulation settings and configurations) and the parameters for the parametric equation(s) that represent the geometric shapes that has been fitted to the volumes of activation associated with set of electrode parameters.

Figure 10:
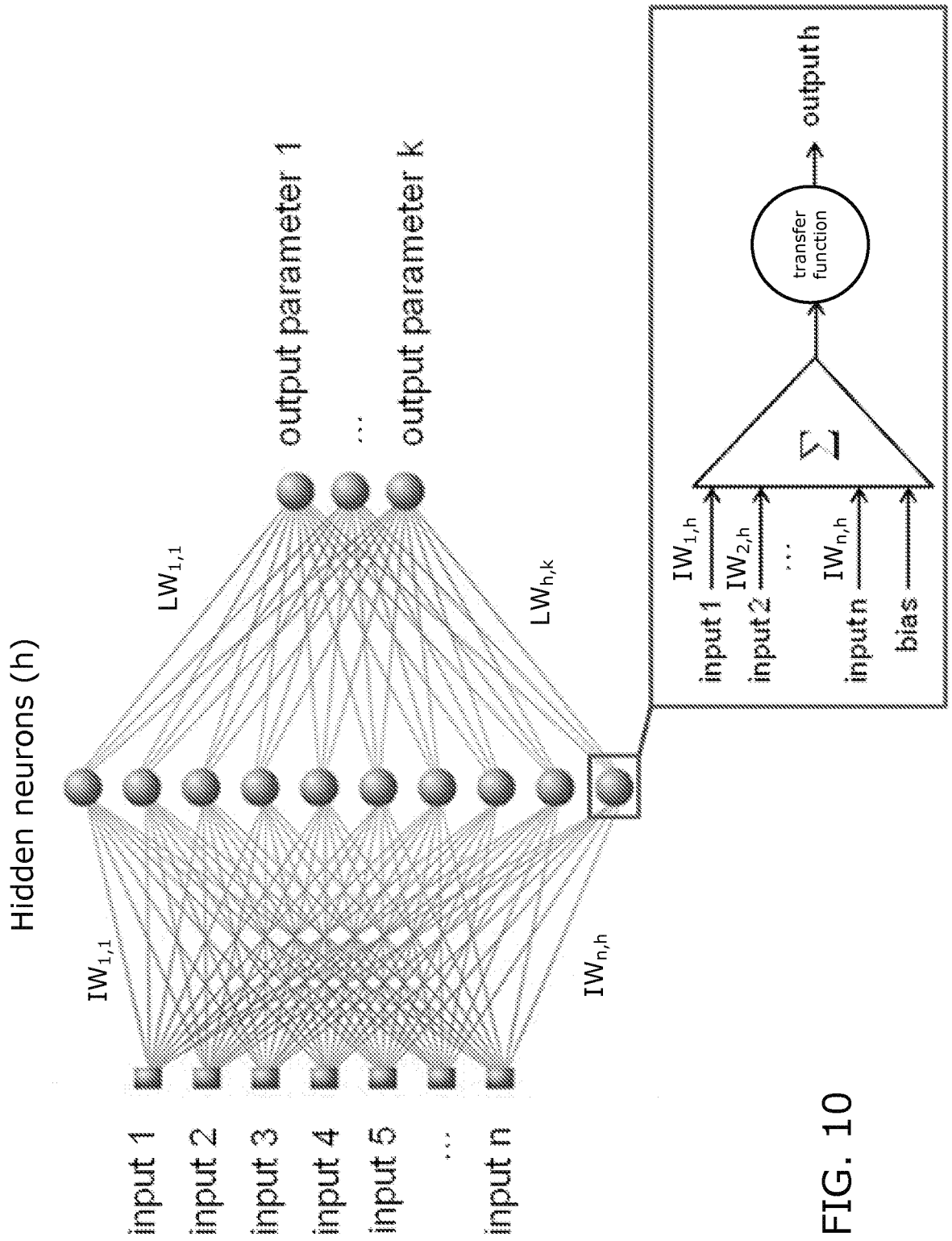
FIG. 10 depicts another example of an artificial neural network that can be used in the present invention.

As explained above, in some cases, the computational training algorithm uses an artificial neural network. The artificial neural network may be used to infer the mapping between the electrode parameters and the parameters of the parametric equation for the geometric shape that has been fitted to the volume of activation that is associated with set of electrode parameters. Using this training data set as the input, the output of the artificial neural network can be used to design a function that maps this relationship. An example of an artificial neural network that can be used in the present invention is shown in FIG. 10. This artificial neural network has three layers: an input layer (the nodes on the left), an output layer (the nodes on the right), and an intermediate, hidden neuron layer (the nodes in the middle). The inset shows how the weights ($W_{n,h}$) and biases are used to change the parameters of the throughput and vary the neural connections in the neural network.

In certain embodiments, the present invention provides a method for determining a function that outputs the parameters of one or more parametric equations that define a volume of activation. The method comprises having an electric field model of an electrode and a neural tissue model. By coupling the electric field model to the neural tissue model as explained above, volumes of activation can be obtained for multiple different sets of stimulation parameters and electrode configuration parameters. A geometric shape (e.g., an ellipsoid), which is defined by one or more parametric equations, is fitted to the volumes of activation. As explained above, this may be performed using an optimization algorithm.

Also as explained above, a computational training algorithm may be used to design a function that correlates the different sets of stimulation parameters and electrode configuration parameters to the parameters for the one or more parametric equations that represent the geometric shapes that are fitted to the volumes of activation. Having designed such a function, this function may be incorporated into computer software (embodied as non-transitory computer-readable storage medium) that comprises instructions for determining the volume of activation using one or more parametric equations whose parameters are given as the function of an input vector that includes stimulation parameters and/or electrode configuration parameters.

Computing Environment

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other processor-based apparatus provide steps for implementing the functions specified in the block or blocks.

Figure 7:
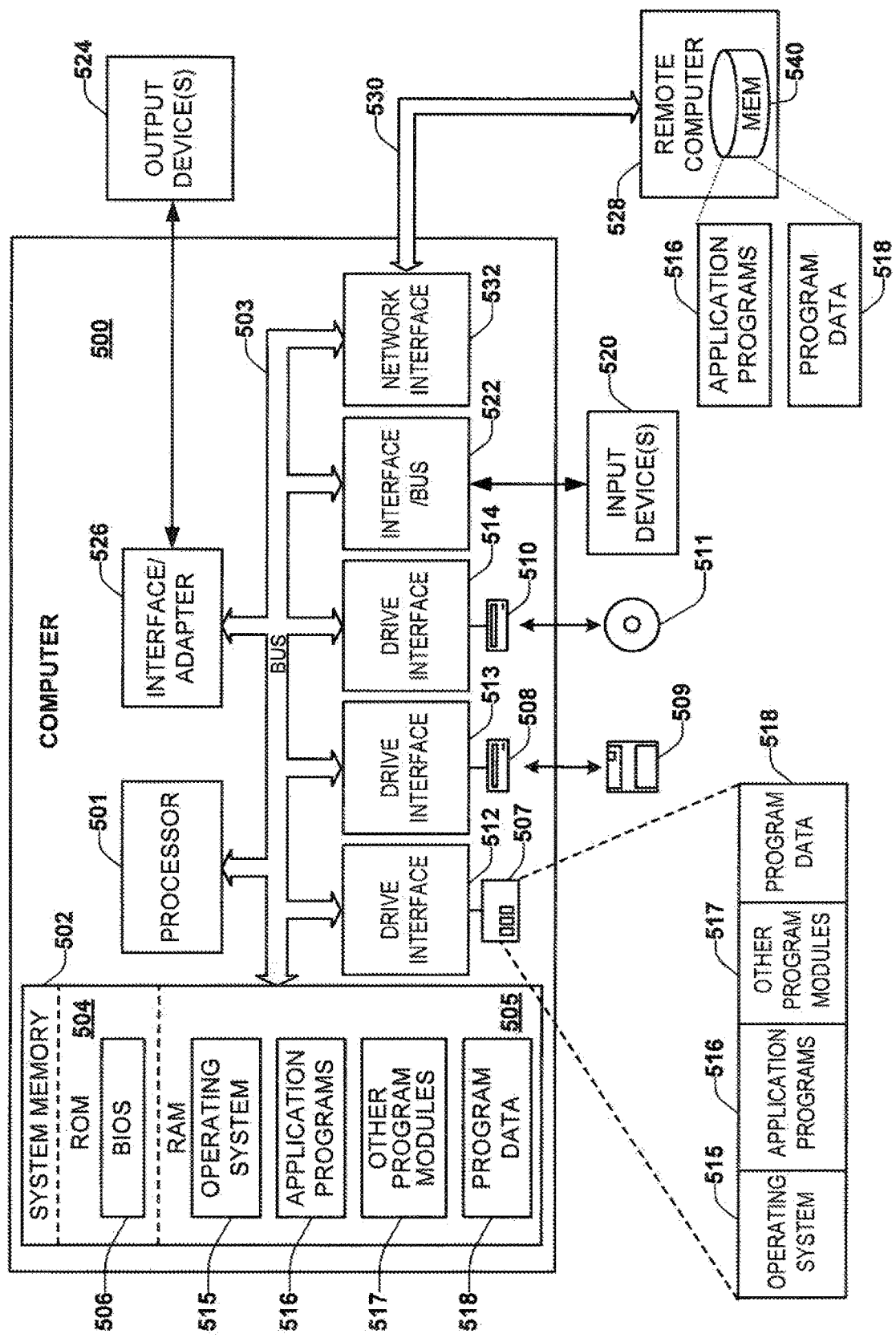
FIG. 7 depicts an example computer environment that can be used to perform methods and processes according to an aspect of the invention.

In this regard, FIG. 7 illustrates one example of a computer system 500 that can be employed to execute one or more embodiments of the invention by storing and/or executing computer executable instructions. Computer system 500 can be implemented on one or more general purpose networked computer systems, embedded computer systems, routers, switches, server devices, client devices, various intermediate devices/nodes or stand alone computer systems. Additionally, computer system 500 can be implemented on various mobile clients such as, for example, a personal digital assistant (PDA), laptop computer, pager, and the like, provided it includes sufficient processing capabilities.

Computer system 500 includes processing unit 501, system memory 502, and system bus 503 that couples various system components, including the system memory, to processing unit 501. Dual microprocessors and other multi-processor architectures also can be used as processing unit 501. System bus 503 may be any of several types of bus structure including a memory bus or memory controller, a peripheral bus, and a local bus using any of a variety of bus architectures. System memory 502 includes read only memory (ROM) 504 and random access memory (RAM) 505. A basic input/output system (BIOS) 506 can reside in ROM 504 containing the basic routines that help to transfer information among elements within computer system 500.

Computer system 500 can include a hard disk drive 507, magnetic disk drive 508, e.g., to read from or write to removable disk 509, and an optical disk drive 510, e.g., for reading CD-ROM disk 511 or to read from or write to other optical media. Hard disk drive 507, magnetic disk drive 508, and optical disk drive 510 are connected to system bus 503 by a hard disk drive interface 512, a magnetic disk drive interface 513, and an optical drive interface 514, respectively. The drives and their associated computer-readable media provide nonvolatile storage of data, data structures, and computer-executable instructions for computer system 500. Although the description of computer-readable media above refers to a hard disk, a removable magnetic disk and a CD, other types of non-transitory computer-readable media that are readable by a computer, such as magnetic cassettes, flash memory cards, digital video disks and the like, in a variety of forms, may also be used in the operating environment; further, any such media may contain computer-executable instructions for implementing one or more parts of the invention. The term "non-transitory computer-readable storage medium" encompasses all computer-readable storage media, with the sole exception being a transitory, propagating signal.

A number of program modules may be stored in drives and RAM 505, including operating system 515, one or more application programs 516, other program modules 517, and program data 518. The application programs and program data can include functions and methods programmed to train a neural network, provide a neural network or otherwise enable a user to interact with or interface with the network via a user interface, such as shown and described herein.

A user may enter commands and information into computer system 500 through one or more input devices 520, such as a pointing device (e.g., a mouse, touch screen), keyboard, microphone, joystick, game pad, scanner, and the like. For instance, the user can employ input device 520 to edit or modify a domain model. Additionally or alternatively, a user can access a user interface via the input device to create one or more instances of a given domain model and associated data management tools, as described herein. These and other input devices 520 are often connected to processing unit 501 through a corresponding port interface 522 that is coupled to the system bus, but may be connected by other interfaces, such as a parallel port, serial port, or universal serial bus (USB). One or more output devices 524 (e.g., display, a monitor, printer, projector, or other type of displaying device) is also connected to system bus 503 via interface 526, such as a video adapter.

Computer system 500 may operate in a networked environment using logical connections to one or more remote computers, such as remote computer 528. Remote computer 528 may be a workstation, computer system, router, peer device, or other common network node, and typically includes many or all the elements described relative to computer system 500. The logical connections, schematically indicated at 530, can include a local area network (LAN) and a wide area network (WAN).

When used in a LAN networking environment, computer system 500 can be connected to the local network through a network interface or adapter 532. When used in a WAN networking environment, computer system 500 can include a modem, or can be connected to a communications server on the LAN. The modem, which may be internal or external, can be connected to system bus 503 via an appropriate port interface. In a networked environment, application programs 516 or program data 518 depicted relative to computer system 500, or portions thereof, may be stored in a remote memory storage device 540.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A system for determining parameters for electrical stimulation, the system comprising:
    a memory having stored thereon processor-executable instructions for a volume of tissue activated (VTA) estimator;
    a processor coupled to the memory configured to, when executing the processor-executable instructions for the VTA estimator, estimate, for each set of stimulation parameter values input into the VTA estimator, a volume of tissue that is activated by electrical stimulation using the set of stimulation parameter values, wherein the VTA estimator comprises a trained artificial intelligence module to estimate the volume of tissue that is activated by electrical stimulation using the set of stimulation parameter values, wherein the trained artificial intelligence module comprises an artificial neural network;
    a user interface coupled to the processor and configured for input of the sets of stimulation parameter values; and
    a display coupled to the processor and the user interface and configured for displaying the estimates generated by the VTA estimator.

2. The system of claim 1, wherein the VTA estimator further comprises a VTA model module.

3. The system of claim 2, wherein the VTA model module comprising at least one parametric equation model that defines a volume of activation.

4. The system of claim 3, wherein at least one of the at least one parametric equation model comprises one or more parametric equations that represent a geometric shape.

5. The system of claim 4, wherein the geometric shape is an ellipsoid shape or a super ellipsoid shape.

6. The system of claim 2, wherein the VTA model module comprises having an electric field model of an electrode.

7. The system of claim 2, wherein the VTA model module comprises a neural tissue model.

8. The system of claim 1, wherein the set of stimulation parameter values comprises a value for each of one or more of pulse width, electrode contact impedance, encapsulation tissue conductivity, voltage, or electrode contact configuration.

9. The system of claim 1, wherein the memory further comprises processor-executable instructions for a correlator, wherein the processor, when executing the processor-executable instructions for the correlator, is configured for correlating a target volume with the estimates generated by the VTA estimator.

10. The system of claim 9, wherein the processor, when executing the processor-executable instructions for the correlator, is configured to provide a score indicative of an amount of overlap between the target volume and a one of the estimates generated by the VTA estimator.

11. A non-transitory computer-readable medium having processor-executable instructions for determining electrical stimulation parameters for providing electrical stimulation to a patient, the processor-executable instructions when installed onto a device enable the device to perform actions, the actions comprising:
    receiving a target volume;
    estimating, for each set of stimulation parameter values, a volume of tissue that is activated by electrical stimulation using the set of stimulation parameter values using a VTA estimator, wherein the VTA estimator comprises a trained artificial intelligence module to estimate the volume of tissue that is activated by electrical stimulation using the set of stimulation parameter values, wherein the trained artificial intelligence module comprises an artificial neural network;

comparing the estimated volumes of tissue with the target volume; and selecting, based on the comparisons, one of the estimated volumes of tissue and the corresponding set of stimulation parameter values.

12. The computer-readable medium of claim 11, wherein the VTA estimator further comprises a VTA model module.

13. The computer-readable medium of claim 12, wherein the VTA model module comprising at least one parametric equation model that defines a volume of activation.

14. The computer-readable medium of claim 13, wherein at least one of the at least one parametric equation model comprises one or more parametric equations that represent a geometric shape.

15. The computer-readable medium of claim 14, wherein the geometric shape is an ellipsoid shape or a super ellipsoid shape.

16. The computer-readable medium of claim 12, wherein the VTA model module comprises having an electric field model of an electrode.

17. The computer-readable medium of claim 12, wherein the VTA model module comprises a neural tissue model.

18. The computer-readable medium of claim 11, wherein the set of stimulation parameter values comprises a value for each of one or more of pulse width, electrode contact impedance, encapsulation tissue conductivity, voltage, or electrode contact configuration.

\* \* \* \* \*